(12) United States Patent
Pazenok et al.

(10) Patent No.: US 8,629,288 B2
(45) Date of Patent: Jan. 14, 2014

(54) METHOD FOR THE REGIOSELECTIVE SYNTHESIS OF 1-ALKY1-3-HALOALKYL-PYRAZOLE-4-CARBOXYLIC ACID DERIVATIVES

(75) Inventors: Sergii Pazenok, Solingen (DE); Norbert Lui, Odenthal (DE); Jens-Dietmar Heinrich, Burscheid (DE); Thomas Wollner, Köln (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 12/919,365

(22) PCT Filed: Feb. 12, 2009

(86) PCT No.: PCT/EP2009/000958
§ 371 (c)(1),
(2), (4) Date: Aug. 25, 2010

(87) PCT Pub. No.: WO2009/106230
PCT Pub. Date: Sep. 3, 2009

(65) Prior Publication Data
US 2011/0009642 A1    Jan. 13, 2011

(30) Foreign Application Priority Data
Feb. 25, 2008    (EP) .................................... 08151891

(51) Int. Cl.
| C07C 251/86 | (2006.01) |
| C07C 231/14 | (2006.01) |
| C07C 243/18 | (2006.01) |
| C07C 229/34 | (2006.01) |
| C07C 255/32 | (2006.01) |
| C07D 231/12 | (2006.01) |
| C07D 231/14 | (2006.01) |

(52) U.S. Cl.
USPC ........................... 548/374.1; 558/391; 560/34

(58) Field of Classification Search
None
See application file for complete search history.

(56) References Cited

U.S. PATENT DOCUMENTS

| 7,358,387 B2 | 4/2008 | Lantzsch et al. |
| 7,521,397 B2 | 4/2009 | Dunkel et al. |
| 7,863,460 B2 | 1/2011 | Aihara et al. |
| 8,044,231 B2 | 10/2011 | Pazenok et al. |
| 2010/0256390 A1* | 10/2010 | Bowden et al. ............ 548/374.1 |

FOREIGN PATENT DOCUMENTS

| EP | 1 854 788 A1 | 11/2007 |
| WO | WO 2005/042468 A1 | 5/2005 |

OTHER PUBLICATIONS

Yakimovich et al., Russian Journal of Organic Chemistry, 2008, 44, 621-623.*
Altenbach, R.J., et al., "Synthesis, Potency, and In Vivo Profiles of Quinoline Containing Histamine $H_3$ Receptor Inverse Agonists," *J. Med Chem* 50:5439-5448, American Chemical Society, United States (2007).
Okada, E., et al., "Facile Synthetic Methods for 3- and 5-Trifluoromethy1-4- Trifluoroacetyl-Pyrazoles and Their Conversion into Pyrazole-4-Carboxilic Acids," *Heterocycles* 34(4):791-798, Elsevier Science B.V. Netherlands (1992).
Wakselman, C. and Tordeux, M., "Acylation of Electron-rich Aromatic Nucleus with Fluorinated Immonium Salts," *J.C.S. Chem. Comm.* 23:956, Heffers Printers Ltd, England (1975).
International Search Report with Written Opinion for International Application No. PCT/EP2009/00958, European Patent Office, Netherlands, mailed Jan. 19, 2011.
International Preliminary Report on Patentability for International Application No. PCT/EP2009/00958, International Bureau of WIPO, Switzerland, mailed Apr. 21, 2011.

* cited by examiner

*Primary Examiner* — Sun Jae Loewe
(74) *Attorney, Agent, or Firm* — Sterne, Kessler, Goldstein & Fox P.L.L.C.

(57) ABSTRACT

The present invention relates to a process for the regioselective synthesis of 1-alkyl-3-halo-alkylpyrazole-4-carboxylic acid derivatives by cyclization of 2,3-disubstituted acrylic acid derivatives, and to the hydrazones formed as intermediates in the process.

11 Claims, No Drawings

METHOD FOR THE REGIOSELECTIVE SYNTHESIS OF 1-ALKY1-3-HALOALKYL-PYRAZOLE-4-CARBOXYLIC ACID DERIVATIVES

The present invention relates to a process for the regioselective synthesis of 1-alkyl-3-halo-alkylpyrazole-4-carboxylic acid derivatives by cyclization of 2,3-disubstituted acrylic acid derivatives, and to the hydrazones formed as intermediates in the process.

2-Dihaloacyl-3-dialkylaminoacrylic esters of the formula II (Y=COOAlk, Z=O) are useful intermediates for the preparation of dihalomethyl-substituted pyrazolylcarboxylic acid derivatives which for their part are precursors of fungicidally active compounds (cf. WO 03/070705).

Pyrazolecarboxylic acid derivatives are usually prepared by reacting acrylic acid derivatives having two leaving groups (Z and A) with hydrazines.

The reaction with the monoalkylhydrazines gives mainly 1-alkylpyrazoles. However, the cyclization is frequently not regioselective. As a consequence, depending on the substrate and the reaction conditions, the unwanted 5-alkylpyrazoles are formed in amounts between 10 and 80% (see Scheme 1).

Scheme 1

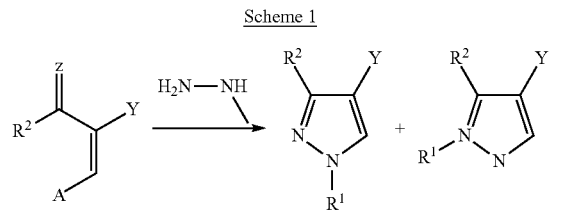

The synthesis of 1-alkylpyrazolecarboxylic acid derivatives by alkylation of pyrazole derivatives unsubstituted in the 1-position frequently also proceeds with formation of both regioisomers (see Scheme 2).

Scheme 2

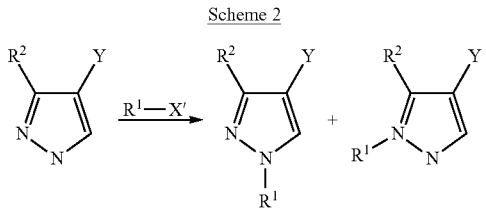

An alternative route of preparing fluorohaloalkylpyrazolecarboxylic acids is the cyclization of, for example, 4,4-dichloro-2-[(dimethylamino)methylidene]-3-oxobutanoate with alkylhydrazines followed by a halogen exchange.

WO 2005/042468 discloses a process for preparing 2-dihaloacyl-3-aminoacrylic esters by reacting acid halides with dialkylaminoacrylic esters, followed by their cyclization with alkylhydrazines.

The European patent application No. 07117232.4, hitherto unpublished, describes a process for preparing HCl-free 2-dihaloacyl-3-aminoacrylic esters by reacting acid fluorides with dialkyl-aminoacrylic acid derivatives. The process can be carried out in the absence of a base, as a result of which the removal of halide salts is not required.

WO 2008/092583 describes a process for preparing 3-dihalomethylpyrazole-4-carboxylic acid derivatives by reacting α,α-fluoroamines in the presence of Lewis acids with acrylic acid derivatives, followed by their reaction with alkylhydrazines.

WO 2006/090778 discloses a process for preparing 1-methyl-3-difluoromethylpyrazole-carboxylic esters by cyclization of 2-alkoxymethylenefluoroacylacetate with methylhydrazine in the presence of water and a base.

However, the processes above-described all have the disadvantage that the cyclization, even at low temperatures, proceeds only with unsatisfactory regioselectivity.

In view of the prior art described above, it is an object of the present invention to provide a process which does not have the disadvantages mentioned above, thus providing regioselective access to 1-alkyl-3-haloalkylpyrazole-4-carboxylic acid derivatives.

The object described above was achieved by a process for preparing 1-alkyl-3-haloalkyl-pyrazole-4-carboxylic acid derivatives of the formula (I)

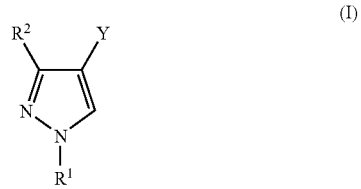

in which $R^1$ is selected from the group consisting of $C_{1-12}$-alkyl, $C_{3-8}$-cycloalkyl, $C_{2-12}$-alkenyl, $C_{2-12}$-alkynyl, $C_{6-8}$-aryl, $C_{7-19}$-arylalkyl and $C_{7-19}$-alkylaryl groups, each of which may be substituted by one or more groups selected from the group consisting of —R', —X', —OR', —SR', —NR'$_2$, —SiR'$_3$, —COOR', —(C=O)R', —CN and —CONR$_2$', where R' is hydrogen or a $C_{1-12}$-alkyl group;

$R^2$ is selected from $C_1$-$C_4$-alkyl groups which may be substituted by one, two or three halogen atoms selected from the group consisting of F, Cl and Br or by a $CF_3$ group;

Y is selected from the group consisting of (C=O)OR$^3$, CN and (C=O)NR$^4$R$^5$, where R$^3$, R$^4$ and R$^5$ independently of one another are selected from the group consisting of $C_{1-12}$-alkyl, $C_{3-8}$-cycloalkyl, $C_{2-12}$-alkenyl, $C_{2-12}$-alkynyl, $C_{6-8}$-aryl, $C_{7-19}$-arylalkyl and $C_{7-19}$-alkylaryl groups, each of which may be substituted by one or more groups selected from the group consisting of —R', —X', —OR', —SR', —NR'$_2$, —SiR'$_3$, —COOR', —(C=O)R', —CN and —CONR$_2$', where R' is hydrogen or a $C_{1-12}$-alkyl group, and R$^4$ and R$^5$ together with the nitrogen atom to which they are attached may form a 5- or 6-membered ring which may optionally contain one or more further heteroatoms selected from the group consisting of O, S and an SO$_2$ group and which may be substituted by one or more groups selected from the group consisting of —R', —X', —OR', —SR', —NR'$_2$, —SiR'$_3$, —COOR', —(C=O)R', —CN and —CONR$_2$', where R' is hydrogen or a $C_{1-12}$-alkyl group;

comprising at least one of the reaction sequences consisting of steps (A) and (D), (B) and (D) or (C) and (D) below:

(A) reaction of a 2-acylated or 2-iminoalkylated acrylic acid derivative of the formula (II),

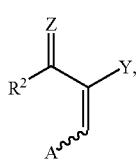

(II)

in which

Z is selected from the group consisting of O, S and $N^+R^{10}R^{11}$, where $R^{10}$ and $R^{11}$ independently of one another are selected from the group consisting of $C_{1-12}$-alkyl, $C_{3-8}$-cycloalkyl, $C_{2-12}$-alkenyl, $C_{2-12}$-alkynyl, $C_{6-8}$-aryl, $C_{7-19}$-arylalkyl and $C_{7-19}$-alkylaryl groups, each of which may be substituted by one or more groups selected from the group consisting of —R', —X', —OR', —SR', —SiR'$_3$, —COOR', —(C=O)R', —CN and —CONR$_2$', where R' is hydrogen or a $C_{1-12}$-alkyl group, and $R^{10}$ and $R^{11}$ together with the nitrogen atom to which they are attached may form a 5- or 6-membered ring which may optionally contain one or two further heteroatoms selected from the group consisting of O, S and an SO$_2$ group and which may be substituted by one or more groups selected from the group consisting of —R', —X', —OR', —SR', —SiR'$_3$, —COOR', —(C=O)R', —CN and —CONR$_2$', where R' is hydrogen or a $C_{1-12}$-alkyl group;

A is a leaving group selected from the group consisting of OR$^{12}$, SR$^{12}$ and NR$^{12}$R$^{13}$, where R$^{12}$ and R$^{13}$ independently of one another are selected from the group consisting of $C_{1-12}$-alkyl, $C_{3-8}$-cycloalkyl, $C_{2-12}$-alkenyl, $C_{2-12}$-alkynyl, $C_{6-8}$-aryl, $C_{7-19}$-arylalkyl and $C_{7-19}$-alkylaryl groups, each of which may be substituted by one or more groups selected from the group consisting of —R', —X', —OR', —SR', —NR'$_2$, —SiR'$_3$, —COOR', —(C=O)R', —CN and —CONR$_2$', where R' is hydrogen or a $C_{1-12}$-alkyl group, and R$^{12}$ and R$^{13}$ together with the nitrogen atom to which they are attached may form a 5- or 6-membered ring which may optionally contain one or two further heteroatoms selected from the group consisting of O, S and an SO$_2$ group and which may be substituted by one or more groups selected from the group consisting of —R', —X', —OR', —SR', —SiR'$_3$, —COOR', —(C=O)R', —CN and —CONR$_2$', where R' is hydrogen or a $C_{1-12}$-alkyl group;

with an N-alkylhydrazone of the formula (III)

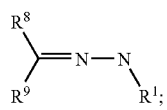

(III)

in which $R^8$ and $R^9$ independently of one another are selected from the group consisting of hydrogen, $C_{3-8}$-cycloalkyl, $C_{2-12}$-alkenyl, $C_{2-12}$-alkynyl, $C_{6-8}$-aryl, $C_{7-19}$-arylalkyl and $C_{7-19}$-alkylaryl groups, each of which may be substituted by one more groups selected from the group consisting of —R', —X', —OR', —SR', —NR'$_2$, —SiR'$_3$, —COOR', —(C=O)R', —CN and —CONR$_2$', where R' is hydrogen or a $C_{1-12}$-alkyl group, and $R^8$ and $R^9$ together with the carbon atom to which they are attached may form a 5- or 6-membered ring which may optionally contain one or two further heteroatoms selected from the group consisting of O, S and an SO$_2$ group and which may be substituted by one or more groups selected from the group consisting of —R', —X$^2$, —OR', —SR', —NR', —CN and —CONR$_2$', where R' is hydrogen or a $C_{1-12}$-alkyl group;

(B) acylation of an acrylic acid hydrazone of the formula (VI);

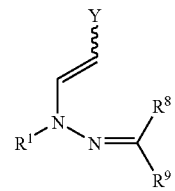

(VI)

with an acyl halide of the formula (X), where X' is selected from the group consisting of F, Cl, Br and I,

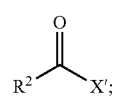

(X)

(C) iminoalkylation of an acrylic acid hydrazone of the formula (VI) above with an α,α-dihaloamine of the formula (XI), where X' is selected from the group consisting of F, Cl, Br and I,

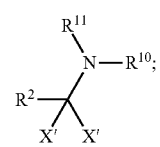

(XI)

(D) cyclization of the intermediates obtained in step (A), (B) or (C) to give the 3-haloalkylpyrazole-4-carboxylic acid derivative of the formula (I), Surprisingly, under the conditions according to the invention, the 1-alkyl-3-haloalkyl-pyrazole-4-carboxylic acid derivatives of the formula (I) can be prepared with good yields, regioselectivities and in high purity, the process according to the invention thus overcoming the disadvantages mentioned above of the preparation processes described in the prior art.

GENERAL DEFINITIONS

In the context of the present invention, the term halogens (X') comprises, unless defined otherwise, elements selected from the group consisting of fluorine, chlorine, bromine and iodine, where fluorine, chlorine and bromine are used with preference and fluorine and chlorine with particular preference.

Optionally substituted groups may be mono- or polysubstituted, where in the case of polysubstitution the substituents may be identical or different.

Alkyl groups substituted by one or more halogen atoms (—X') are, for example, selected from the group consisting of trifluoromethyl (CF$_3$), difluoromethyl (CHF$_2$), CF$_3$CH$_2$, ClCH$_2$, CF$_3$CCl$_2$.

In the context of the present invention, unless defined otherwise, alkyl groups are straight-chain or branched hydrocarbon groups which may optionally have one, two or more heteroatoms selected from the group consisting of O, N, P and S. Moreover, the alkyl groups according to the invention may optionally be substituted by further groups selected from the group consisting of —R', halogen (—X'), alkoxy (—OR'), thioether or mercapto (—SR'), amino (—NR'$_2$), silyl (—SiR'$_3$), carboxyl (—COOR'), cyano (—CN), acyl (—(C═O)R') and amide (—CONR$_2$') groups, where R' is hydrogen or a $C_{1-12}$-alkyl group, preferably a $C_{2-10}$-alkyl group, particularly preferably a $C_{3-8}$-alkyl group, which may have one or more heteroatoms selected from the group consisting of N, O, P and S.

In the context of the present invention, cycloalkyl groups are, unless defined otherwise, monocyclic saturated hydrocarbon groups having 3 to 8 carbon ring members, which groups may optionally contain one, two or more heteroatoms selected from the group consisting of O, N, P and S. Moreover, the cycloalkyl groups according to the invention may optionally be substituted by further groups selected from the group consisting of —R', halogen (—X'), alkoxy (—OR'), thioether or mercapto (—SR'), amino-(—NR'$_2$), silyl (—SiR'$_3$), carboxyl (—COOR'), cyano (—CN), acyl (—(C═O)R') and amide (—CONR$_2$') groups, where R' is hydrogen or a $C_{1-12}$-alkyl group, preferably a $C_{2-10}$-alkyl group, particularly preferably a $C_{3-8}$-alkyl group, which may contain one or more heteroatoms selected from the group consisting of N, O, P and S.

Specifically, this definition comprises, for example, the meanings cyclopropyl, cyclobutyl, cyclopentyl and cyclohexyl.

The definition $C_1$-$C_{12}$-alkyl comprises the largest range defined herein for an alkyl group. Specifically, this definition comprises, for example, the meanings methyl, ethyl, n-, iso-propyl, n-, iso-, sec- and t-butyl, n-pentyl, n-hexyl, 1,3-dimethylbutyl, 3,3-dimethylbutyl, n-heptyl, n-nonyl, n-decyl, n-undecyl, n-dodecyl.

In the context of the present invention, alkenyl groups are, unless defined otherwise, straight-chain or branched hydrocarbon groups which contain at least one single unsaturation (double bond) and may optionally have one, two or more single or double unsaturations or one, two or more heteroatoms selected from the group consisting of O, N, P and S. Moreover, the alkenyl groups according to the invention may optionally be substituted by further groups selected from the group consisting of —R', halogen —X'), alkoxy (—OR'), thioether or mercapto (—SR'), amino (—NR'$_2$), silyl (—SiR'$_3$), carboxyl (—COOR'), cyano (—CN), acyl (—(C═O)R') and amide (—CONR$_2$') groups, where R' is hydrogen or a $C_{1-12}$-alkyl group, preferably a $C_{2-10}$-alkyl group, particularly preferably a $C_{3-8}$-alkyl group, which may contain one or more heteroatoms selected from the group consisting of N, O, P and S.

The definition $C_2$-$C_{12}$-alkenyl comprises the largest range defined herein for an alkenyl group. Specifically, this definition comprises, for example, the meanings vinyl; allyl (2-propenyl), isopropenyl (1-methylethenyl); but-1-enyl (crotyl), but-2-enyl, but-3-enyl; hex-1-enyl, hex-2-enyl, hex-3-enyl, hex-4-enyl, hex-5-enyl; hept-1-enyl, hept-2-enyl, hept-3-enyl, hept-4-enyl, hept-5-enyl, hept-6-enyl; oct-1-enyl, oct-2-enyl, oct-3-enyl, oct-4-enyl, oct-5-enyl, oct-6-enyl, oct-7-enyl; non-1-enyl, non-2-enyl, non-3-enyl, non-4-enyl, non-5-enyl, non-6-enyl, non-7-enyl, non-8-enyl; dec-1-enyl, dec-2-enyl, dec-3-enyl, dec-4-enyl, dec-5-enyl, dec-6-enyl, dec-7-enyl, dec-8-enyl, dec-9-enyl; undec-1-enyl, undec-2-enyl, undec-3-enyl, undec-4-enyl, undec-5-enyl, undec-6-enyl, undec-7-enyl, undec-8-enyl, undec-9-enyl, undec-10-enyl; dodec-1-enyl, dodec-2-enyl, dodec-3-enyl, dodec-4-enyl, dodec-5-enyl, dodec-6-enyl, dodec-7-enyl, dodec-8-enyl, dodec-9-enyl, dodec-10-enyl, dodec-11-enyl; buta-1,3-dienyl, penta-1,3-dienyl.

In the context of the present invention, cycloalkenyl groups are, unless defined otherwise, monocyclic nonaromatic hydrocarbon groups having 3 to 8 carbon ring members and at least one double bond, which groups may optionally contain one, two or more heteroatoms selected from the group consisting of O, N, P and S. Moreover, the cycloalkenyl groups according to the invention may optionally be substituted by further groups selected from the group consisting of —R', halogen (—X'), alkoxy (—OR'), thioether or mercapto (—SR'), amino (—NR'$_2$), silyl (—SiR'$_3$), carboxyl (—COOR'), cyano (—CN), acyl (—(C═O)R') and amide (—CONR$_2$') groups, where R' is hydrogen or a $C_{1-12}$-alkyl group, preferably a $C_{2-10}$-alkyl group, particularly preferably a $C_{3-8}$-alkyl group, which may contain one or more heteroatoms selected from the group consisting of N, O, P and S.

Specifically, this definition comprises, for example, the meanings cyclopenten-1-yl, cyclohexen-1-yl, cyclohepta-1,3-dien-1-yl.

In the context of the present invention, alkynyl groups are, unless defined otherwise, straight-chain, branched or cyclic hydrocarbon groups which contain at least one double unsaturation (triple bond) and may optionally have one, two or more single or double unsaturations or one, two or more heteroatoms selected from the group consisting of O, N, P and S. Moreover, the alkynyl groups according to the invention may optionally be substituted by further groups selected from the group consisting of —R', halogen (—X'), alkoxy (—OR'), thioether or mercapto (—SR'), amino (—NR'$_2$), silyl (—SiR'$_3$), carboxyl (—COOR'), cyano (—CN), acyl (—(C═O)R') and amide (—CONR$_2$') groups, where R' is hydrogen or a straight-chain, branched or cyclic $C_{1-12}$-alkyl group which may contain one or more heteroatoms selected from the group consisting of N, O, P and S.

The definition $C_2$-$C_{12}$-alkynyl comprises the largest range defined herein for an alkynyl group. Specifically, this definition comprises, for example, the meanings ethynyl(acetylenyl); prop-1-inyl and prop-2-inyl.

In the context of the present invention, aryl groups are, unless defined otherwise, aromatic hydrocarbon groups which may contain one, two or more heteroatoms selected from the group consisting of O, N, P and S and which may optionally be substituted by further groups selected from the group consisting of —R', halogen (—X'), alkoxy (—OR'), thioether or mercapto (—SR'), amino (—NR'$_2$), silyl (—SiR'$_3$), carboxyl (—COOR'), cyano (—CN), acyl (—(C═O)R') and amide (—CONR$_2$') groups, where R' is hydrogen or a $C_{1-12}$-alkyl group, preferably a $C_{2-10}$-alkyl group, particularly preferably a $C_{3-8}$-alkyl group, which may contain one or more heteroatoms, selected from the group consisting of N, O, P and S.

The definition $C_{5-18}$-aryl comprises the largest range defined herein for an aryl groups having 5 to 18 skeleton atoms, where the carbon atoms may be replaced by heteroatoms. Specifically, this definition comprises, for example, the meanings cyclopentadienyl, phenyl, cyclohepta-trienyl, cyclooctatetraenyl, naphthyl and anthracenyl; 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-thiazol-2-yl; 1-pyrrolyl, 1-pyrazolyl, 1,2,4-triazol-1-yl, 1-imidazolyl, 1,2,3-triazol-1-yl, 1,3,4-triazol-1-yl; 3-pyridazinyl, 4-pyridazinyl, 2-pyrimidinyl, 4-pyrimidinyl, 5-pyrimidinyl 2-pyrazinyl, 1,3,5-triazin-2-yl and 1,2,4-triazin-3-yl.

In the context of the present invention, arylalkyl groups (aralkyl groups) are, unless defined otherwise, alkyl groups which are substituted by aryl groups, which may have a $C_{1-8}$-alkylene chain and which may be substituted in the aryl skeleton or the alkylene chain by one or more heteroatoms selected from the group consisting of O, N, P and S and optionally by further groups selected from the group consisting of —R', halogen-(—X'), alkoxy (—OR'), thioether or mercapto (—SR'), amino (—NR'$_2$), silyl (—SiR'$_3$), carboxyl (—COOR'), cyano (—CN), acyl (—(C=O)R') and amide (—CONR$_2$') groups, where R' is hydrogen or a $C_{1-12}$-alkyl group, preferably a $C_{2-10}$-alkyl group, particularly preferably a $C_{3-8}$-alkyl group, which may contain one or more heteroatoms selected from the group consisting of N, O, P and S.

The definition $C_{7-19}$-aralkyl group comprises the largest range defined herein for an arylalkyl group having a total of 7 to 19 atoms in the skeleton and the alkylene chain. Specifically, this definition comprises, for example, the meanings benzyl and phenylethyl.

In the context of the present invention, alkylaryl groups (alkaryl groups) are, unless defined otherwise, aryl groups which are substituted by alkyl groups, which may have a $C_{1-8}$-alkylene chain and which may be substituted in the aryl skeleton or the alkylene chain by one or more heteroatoms selected from the groups consisting of O, N, P and S and optionally by further groups selected from the group consisting of —R', halogen (—X'), alkoxy (—OR'), thioether or mercapto (—SR'), amino (—NR'$_2$), silyl (—SiR'$_3$), carboxyl (—COOR'), cyano (—CN), acyl (—(C=O)R') and amide (—CONR$_2$') groups, where R' is hydrogen or a $C_{1-12}$-alkyl group, preferably a $C_{2-10}$-alkyl group, particularly preferably a $C_{3-8}$-alkyl group, which may contain one or more heteroatoms selected from the group consisting of N, O, P and S.

The definition $C_{7-19}$-alkylaryl group comprises the largest range defined herein for an alkylaryl group having a total of 7 to 19 atoms in the skeleton and the alkylene chain. Specifically, this definition comprises, for example, the meanings tolyl, 2,3-, 2,4-, 2,5-, 2,6-, 3,4- or 3,5-dimethylphenyl.

The alkyl, alkenyl, alkynyl, aryl, alkaryl and aralkyl groups may furthermore contain one or more heteroatoms which—unless defined otherwise—are selected from the group consisting of N, O, P and S. Here, the heteroatoms replace the carbon atoms specified.

If appropriate, the compounds according to the invention can be present as mixtures of various possible isomeric forms, in particular of stereoisomers, such as, for example, E and Z, threo and erythro and also optical isomers, and, if appropriate, also of tautomers. What is disclosed and claimed are both the E and the Z isomers, and also the threo and erythro isomers and the optical isomers, any mixtures of these isomers, and also the possible tautomeric thrms.

Scheme 3 below summarizes the individual variants of the process according to the invention:

Scheme 3

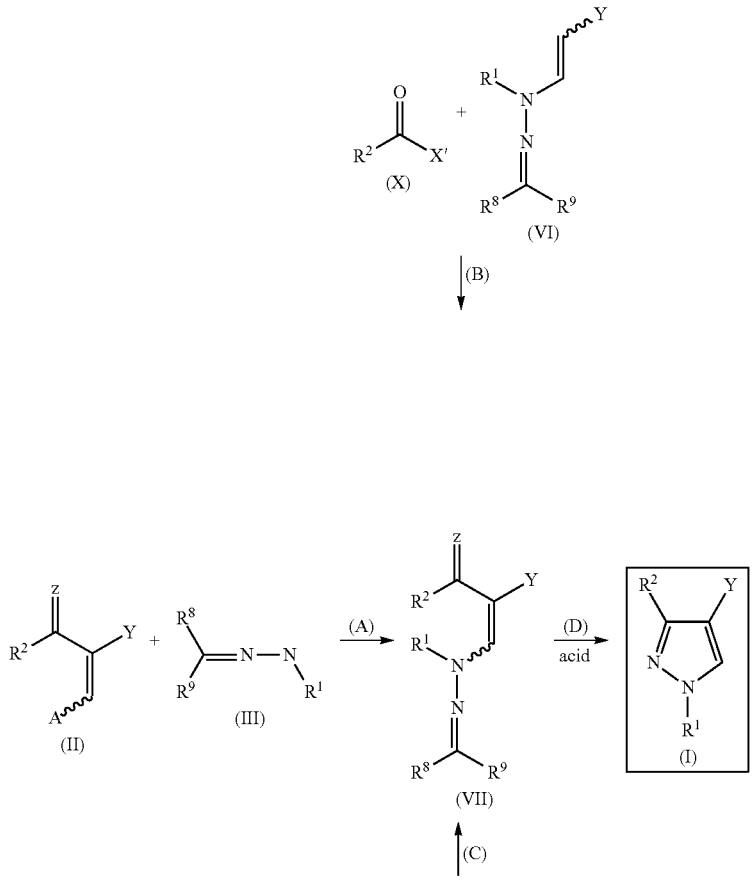

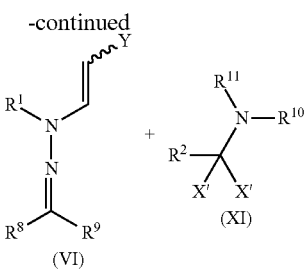

The 1-alkyl-3-haloalkylpyrazole-4-carboxylic acid derivatives obtainable by the process according to the invention are compounds of the formula (I)

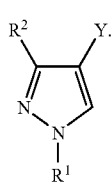

According to the invention, the radicals in formula (I) have the meanings below:

$R^1$ is selected from the group consisting of $C_{1-12}$-alkyl, $C_{3-8}$-cycloalkyl, $C_{2-1G}$ alkenyl, $C_{2-12}$-alkynyl, $C_{6-8}$-aryl, $C_{7-19}$-arylalkyl and $C_{7-19}$-alkylaryl groups, each of which may be substituted by one or more groups selected from the group consisting of —R', —OR', —SR', —NR'$_2$, -cow, —(C=O)R', —CN and —CONR$_2$', where R' is hydrogen or a $C_{1-42}$-alkyl group;

$R^2$ is selected from $C_1$-$C_4$-alkyl groups which may be substituted by one, two or three halogen atoms selected from the group consisting of F, Cl and Br or by a $CF_3$ group;

Y is selected from the group consisting of (C=O)OR$^3$, CN and (C=O)NR$^4$R$^5$, where R$^3$, R$^4$ and R$^5$ independently of one another are selected from the group consisting of $C_{1-12}$-alkyl, $C_{3-8}$-cycloalkyl, $C_{2-12}$-alkenyl, $C_{2-12}$-alkynyl, $C_{6-8}$-aryl, $C_{7-19}$-arylalkyl and $C_{7-19}$-alkylaryl groups, each of which may be substituted by one or more groups selected from the group consisting of —R', —X', —OR', —SR', —NR'$_2$, —SiR'$_3$, —COOR', —(C=O)R', —CN and —CONR$_2$', where R' is hydrogen or a $C_{1-12}$-alkyl group, and R$^4$ and R$^5$ together with the nitrogen atom to which they are attached may form a 5- or 6-membered ring which may optionally contain one or more further heteroatoms selected from the group consisting of O, S and an $SO_2$ group and which may be substituted by one or more groups selected from the group consisting of —R', —X', —OR', —SR', —NR'$_2$, —SiR'$_3$, —COOR', —(C=O)R', —CN and —CONR$_2$', where R' is hydrogen or a $C_{1-12}$-alkyl group.

in a preferred embodiment of the present invention, the radicals in formula (I) have the meanings below:

$R^1$ is selected from the group consisting of methyl, ethyl, n-propyl and isopropyl, $R^2$ is selected from the group consisting of chloromethyl, bromomethyl, dichloromethyl, trichloromethyl, fluoromethyl, difluoromethyl, trifluoromethyl, chlorofluoromethyl, dichlorofluoromethyl, dilorodifluoromethyl, 1-chloroethyl, 1-bromoethyl, ethyl, 2-fluoroethyl, 2,2-difluoroethyl, 2,2,2-trifluoroethyl, 2-chloro-2-fluoroethyl, 2-chloro-2-difluoroethyl, 2,2-dichloro-2-fluoroethyl, 2,2,2-trichloroethyl, pentafluoroethyl and 1,1,1-trifluoroprop-2-yl; 1,2,2,2-tetrafluoroethyl, Y is selected from the group consisting of (C=O)OR$^3$, CN and (C=O)NR$^4$R$^5$, where R$^3$, R$^4$ and R$^5$ independently of one another are selected from the group consisting of methyl, ethyl, n-propyl and isopropyl.

In a particularly preferred embodiment of the present invention, the radicals in formula (I) have the meanings below:

$R^1$ is methyl, $R^2$ is selected from the group consisting of trifluoromethyl and difluoromethyl, Y is selected from the group consisting of (C=O)OR$^3$, where R$^3$ is methyl or ethyl.

Step (A)

In a first embodiment of the present process, which is the result of combining reaction steps (A) and (D), initially 2-acylated or 2-iminoalkylated acrylic acid derivatives of the formula (II) are reacted with N-alkylhydrazones of the formula (III) (Scheme 4). Subsequently, the intermediates formed in step (A) are cyclized to give the 3-haloalkylpyrazole-4-carboxylic acid derivatives of the formula (I) (Step D).

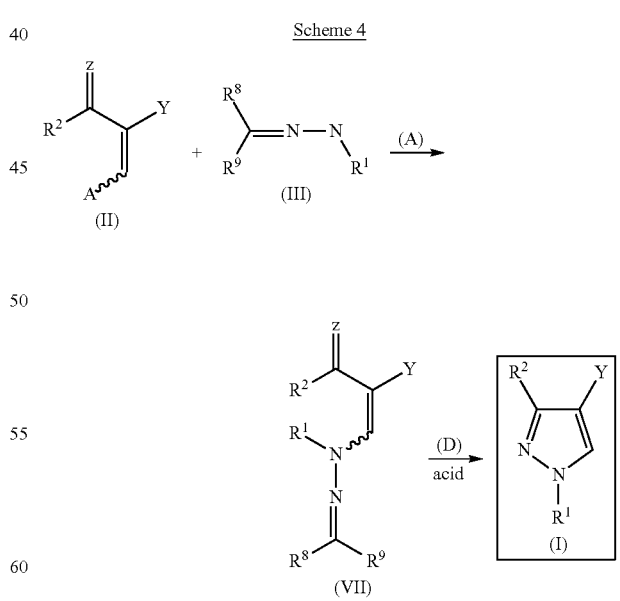

Scheme 4

Possible intermediates which may, in accordance with the present invention, result from reaction step (A) are the acrylhydrazones of the formula (VII)

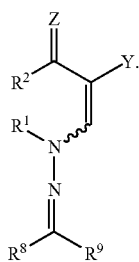

(VII)

This formula includes in particular the 2-acylhydrazinoprop-2-enoates of the formula (VIIa) and the hydrazinoaminium salts of the formula (VIIb)

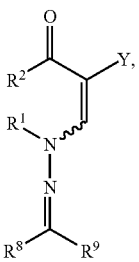

(VIIa)

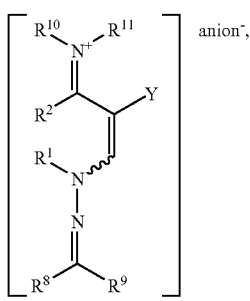

(VIIb)

in which the radicals $R^1$, $R^2$, $R^8$ to $R^{11}$ and Y have the meanings described above and which optionally have a counterion (anion) selected from the group consisting of $Cl^-$, $BF_4^-$, $PF_6^-$, $SbF_6^-$ and $AlCl_4^-$.

The process step (A) according to the invention is preferably carried out in a temperature range of from −20° C. to +150° C., particularly preferably at temperatures of from −10° C. to +70° C.

The process step (A) according to the invention is generally carried out under atmospheric pressure. However, alternatively, it is also possible to operate under reduced pressure to remove the highly volatile dialkylamines.

The reaction time is not critical and may, depending on the batch size and the temperature, be chosen from a range of between a few minutes and a number of hours.

When carrying out the process step (A) according to the invention, 1 mol of the acrylic acid derivative of the formula (II) is reacted with from 0.5 mol to 3 mol, preferably from 0.5 mol to 1.5 mol, particularly preferably with an equimolar amount, of the hydrazone of the formula (III).

Preferably, the hydrazone of the formula (III, dissolved in the solvent, is initially charged, and the acrylic acid derivative of the formula (II) is added. However, it is also possible to reverse the order.

The reaction can be promoted by adding catalysts, such as, for example, $CH_3COOH$, $H_2SO_4$, $KHSO_4$, $NaH_2PO_4$, HCl, $CF_3COOH$, $CH_3COONa$.

Work-up and isolation of the intermediates is generally not required, and the reaction mixture obtainable from step (A) can be used immediately or after storage for the cyclization step (D).

The acrylic acid derivatives of the formula (II) can be obtained by the processes described above, in connection with the prior art.

In the context of the present invention, preference is given to using 2-acylated or 2-iminoalkylated acrylic acid derivatives of the formula (II) selected from the group consisting of ethyl (2-ethoxymethylene)-4,4-difluoromethylacetoacetate, ethyl-(2-ethoxymethylene)-4,4,4-trifluoromethylacetonitrile, 2-[(dimethylamino)methylidene]-4,4,4-trifluoro-3-oxobutanenitrile, N-1-(trifluoromethyl)-3-(dimethylamino)-2-(ethoxycarbonypprop-2-en-1-ylidene]-N-methyl-methanaminium chloride, ethyl 2-(difluoroacetyl)-3-(dimethylamino)acrylate, N-1-(difluoromethyl)-3-(dimethylamino)-2-(ethoxycarbonyl)prop-2-en-1-ylidene]-N-methyl-methanaminium tetrafluoroborate and N-[3-(dimethylamino)-2-(ethoxycarbonyl)-1-(1,1,2,2-tetrafluoroethyl)prop-2-en-1-ylidene]-N-methylmethanaminium chloride.

In the context of the present invention, the N-alkylhydrazones of the formula (III) are preferably selected from the group consisting of 1-methyl-2-(1-methylethylidene)hydrazine, 1-methyl-2-(1,2,2-trimethylpropylidene)hydrazine, 1-methyl-2-(1-methylpropylidene)hydrazine, 1-cyclohexylidene-2-methylhydrazine, 1-methyl-2-(phenylmethylidene) hydrazine, 1-methyl-2-(1-phenylethylidene)hydrazine, 1-(diphenylmethylidene)-2-methylhydrazine en ethyl-2 [(dimethylamino)methylidene]-4,44-trifluoro-3-oxo-butanoat.

The N-alkylhydrazones of the formula (III) have been described in the literature (Zhurnal Organicheskoi Khimii (1968), 4(6), 986-92.) and can be obtained by reacting commercially available hydrazines of the formula (VIII) with carbonyl compounds of the formula (IX) (see Scheme 5).

Scheme 5

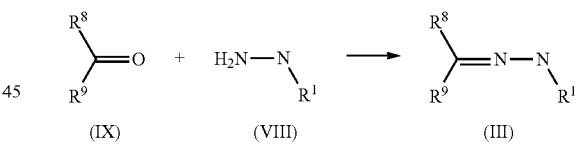

(IX)    (VIII)    (III)

According to the invention, the radicals in formulae (III), (VIII) and (IX) have the meanings below:

$R^1$ is selected from the group consisting of $C_{1-12}$-alkyl, $C_{3-8}$-cycloalkyl, $C_{2-12}$-alkenyl, $C_{2-12}$-alkynyl, $C_{6-8}$-aryl, $C_{7-19}$-arylalkyl and $C_{7-19}$-alkylaryl groups, each of which may be substituted by one or more groups selected from the group consisting of —R', —X', —OR', —SR', —NR'$_2$, —SiR'$_3$, —COOR', —(C=O)R', —CN and —CONR$_2$', where R' is hydrogen or a $C_{1-12}$-alkyl group;

$R^8$ and $R^9$ independently of one another are selected from the group consisting of hydrogen, $C_{1-12}$-alkyl, $C_{3-8}$-cycloalkyl, $C_{2-12}$-alkenyl, $C_{2-12}$-alkynyl, $C_{6-8}$-aryl, $C_{7-19}$-arylalkyl and $C_{7-19}$-alkylaryl groups, each of which may be substituted by one more groups selected from the group consisting of —R', —X', —OR', —SR', —NR'$_2$, —SiR'$_3$, —COOR', —(C=O)R', —CN and —CONR$_2$', where R' is hydrogen or a $C_{1-12}$-alkyl group, and $R^8$ and $R^9$ together with the carbon atom to which they are attached may form a 5- or 6-membered ring which may optionally contain one or two further heteroatoms selected from the group consisting of O, S and an $SO_2$ group and which may be substituted by one or more groups selected from the group consisting of —R', —X', —OR', —SR', —NR'$_2$, —SiR'$_3$, —COOR', —(C=O)R', —CN and —CONR$_2$', where R' is hydrogen or a $C_{1-12}$-alkyl group.

According to the invention, the radicals in formulae (III), (VIII) and (IX) have the preferred meanings below:

$R^1$ is methyl, ethyl, n-propyl, isopropyl, n-butyl, sec-butyl, tert-butyl;

$R^8$ is selected from the group consisting of H, methyl, ethyl, n-propyl, isopropyl, n-butyl, sec-butyl, tert-butyl, phenyl, tolyl, cyclohexyl;

$R^9$ is selected from the group consisting of H, methyl, ethyl, n-propyl, isopropyl, n-butyl, sec-butyl, tert-butyl, phenyl, tolyl, cyclohexyl.

Alternatively, $R^8$ and $R^9$ together with the carbon atom to which they are attached may form a 5- or 6-membered ring.

According to the invention, the radicals in formulae (III), (VIII) and (IX) have the following particularly preferred meanings:

$R^1$ is methyl;

$R^8$ is selected from the group consisting of H, methyl, tert-butyl, phenyl;

$R^9$ is selected from the group consisting of H, methyl, tert-butyl, phenyl.

According to the invention, preference is given to using ketones of the formula (IX) selected from the group consisting of acetone, benzophenone, pinacolone, cyclohexanone, benzaldehyde, with acetone and benzaldehyde being particularly preferably used.

A further advantage of the process according to the invention is the fact that, to prepare the N-methylhydrazones of the formula (III), it is possible to use aqueous methylhydrazine solutions and the explosive concentrated methylhydrazine, which is also used as rocket fuel, is not necessarily required.

In two further embodiments of the process according to the invention which result when the reactions steps (B) and (D) or (C) and (D) are combined, acrylic acid derivatives of the formula (VI) are acylated (step (B)) or iminoalkylated (step (C) and finally cyclized to give the 3-halo-alkylpyrazole-4-carboxylic acid derivatives of the formula (I) (step D).

Step (B): Acylation

In one embodiment of the process according to the invention, the acrylic acid hydrazones of the formula (VI) are acylated with haloalkylcarbonyl halides of the formula (X) according to Scheme 6 below to give the 2-acylacrylic acid hydrazones of the formula (VIIa). In formula (X), $R^2$ has the above meanings and X' is a halogen atom selected from the group consisting of F, Cl or Br, preferably from the group consisting of F and Cl, particularly preferably F.

In the context of the present invention, the acylating agent used is preferably a haloalkylcarbonyl halide of the formula (X) selected from the group consisting of difluoroacetyl chloride, difluoroacetic anhydride, difluoroacetyl fluoride, trifluoroacetyl chloride and trifluoroacetyl fluoride.

The acrylic acid hydrazones of the formula (VI) used in step (B) are preferably selected from the group consisting of ethyl (2E)-3-[1-methyl-2-(propan-2-ylidene)hydrazinyl]prop-2-enoate, ethyl (2Z)-3-[1-methyl-2-(propan-2-ylidene)hydrazinyl]prop-2-enoate, methyl 3-[1-methyl-2-(propan-2-ylidene)hydrazinyl]prop-2-enoate, propyl 3-[1-methyl-2-(propan-2-ylidene)-hydrazinyl]prop-2-enoate, ethyl (2E)-3-[1-methyl-2-(3,3-dimethylbutan-2-ylidene)hydrazinyl]prop-2-enoate, methyl 3-[1-methyl-2-(3,3-dimethylbutan-2-ylidene)hydrazinyl]prop-2-enoate, methyl 3-[1-methyl-2-(phenylmethylidene)hydrazinyl]prop-2-enoate, (2E)-3-[1-methyl-2-(phenylmethylidene)hydrazinyl]prop-2-enenitile and methyl 3-[1-ethyl-2-(propan-2-ylidene)-hydrazinyl]prop-2-enoate.

Scheme 6

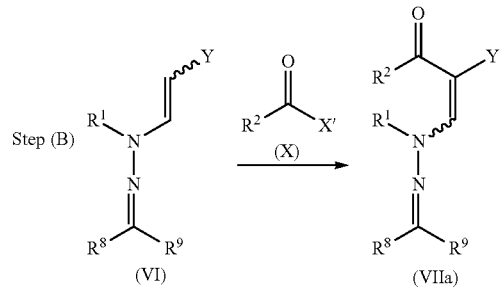

According to the invention, the acylation is carried out at temperatures of from –20° C. to +150° C., preferably at temperatures of from –20° C. to +100° C., particularly preferably at from –10 to 50° C., and under atmospheric pressure.

The reaction time is not critical and may, depending on the batch size and the temperature, be chosen from a range between a few minutes and a number of hours.

According to the invention, 1 mol of the acrylic acid hydrazone of the formula (VI) is reacted with from 0.5 mol to 3 mol, preferably from 1.2 mol to 1.5 mol, particularly preferably with equimolar amounts, of the haloalkylcarbonyl halide of the formula (X).

Preferably, the hydrazinoacrylic acid derivative of the formula (VI) dissolved in the solvent is initially charged, and the haloalkylcarbonyl halide of the formula (X) is added. However, a reverse order is also possible.

The acylation is preferably carried out in the presence of a base. Preference is given here to organic bases, such as trialkylamines, alkylpyridines, phosphazenes and 1,8-diazabicyclo[5.4.0]undecene (DBU); alkali metal hydroxides, such as, for example, lithium hydroxide, sodium hydroxide or potassium hydroxide, alkali metal carbonates ($Na_2CO_3$, $K_2CO_3$) and alkoxides, such as, for example, NaOMe, NaOEt, NaOt-Bu, KOt-Bu.

Suitable solvents are, for example, aliphatic, alicyclic or aromatic hydrocarbons, such as, for example, petroleum ether, n-hexane, n-heptane, cyclohexane, methylcyclohexane, benzene, toluene, xylene or decaline, and halogenated hydrocarbons, such as, for example, chloro-benzene, dichlorobenzene, dichloromethane, chloroform, carbon tetrachloride, dichloroethane or trichloroethane, ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles, such as acetonitrile, propionitrile, n- or isobutyronitrile or benzonitrile; ketones, such as acetone, methyl ethyl ketone, methyl isobutyl ketone or cyclohexanone; amides, such as N,N-dimethylformamide, N,N-dimethylacetamide, N-methylformanilide, N-methylpyrrolidone or hexamethylphosphoric triamide; sulphoxides, such as dimethyl sulphoxide, or sulphones, such as sulpholane. Particular preference is given to using toluene, xylene, chlorobenzene, n-hexane, cyclohexane or methylcyclohexane, very particularly preferably toluene or xylene.

Possible intermediates which, according to the present invention, may result from reaction step (B) are, usually, the 2-acylhydrazinoacrylic acid derivatives of the formula (VIIa).

The intermediates formed can, without prior work-up, be used for the cyclization step (step D).

Alternatively, the intermediates can be isolated by suitable work-up steps and, if appropriate, further purification, and they can be used at a later point in time for the cyclization (step D).

The acrylic acid hydrazones of the formula (VI) have been described in the literature (see Chem. Ber. 1975, 108 (7), 2161-2170; Bulletin de la Societe Chimique de France (1976), (1-2, Pt. 2), 260-4), and they can be prepared according to Scheme 7 or 8 below.

Scheme 7

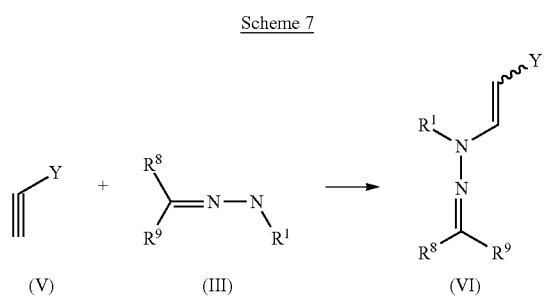

Scheme 8

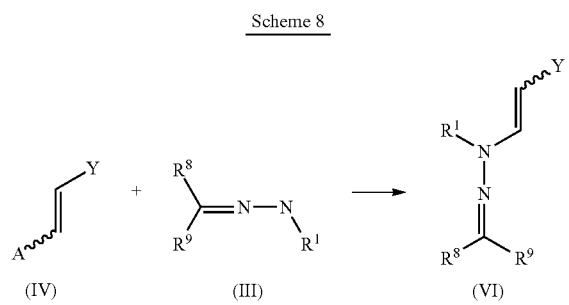

Step (C) Iminoalkylation

In a further embodiment of the process according to the invention, the acrylic acid hydrazones of the formula (VI) are iminoalkylated with at least one α,α-dihaloamine of the formula (XI), according to Scheme 9 below to give the hydrazinoaminium salts of the formula (VIIb). formula (XI), X' and $R^2$ have the above meanings.

Scheme 9

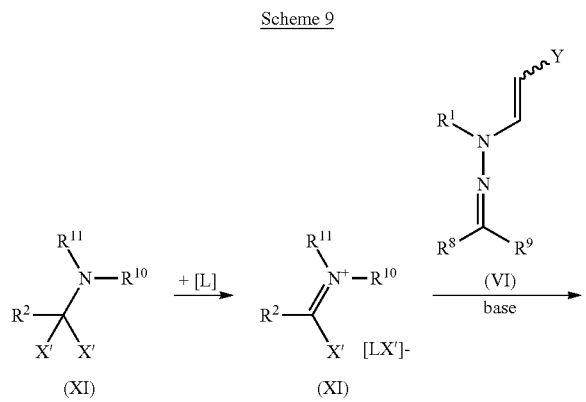

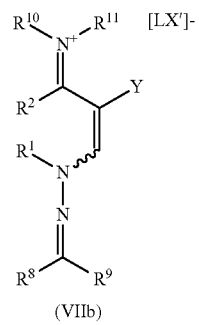

(VIIb)

In Scheme 9 [L] is a Lewis acid.

In the context of the present invention, the iminoalkylating agent of the formula (XI) used may be 1,1,2,2-tetrafluoroethyl-N,N-dimethylamine, 1,1,2,2-tetrafluoroethyl-N,N-diethylamine, 1,1,2-trifluoro-2-(trifluoromethyl)ethyl-N,N-dimethylamine, 1,1,2-trifluoro-2-(trifluoromethyl)-ethyl-N,N-diethylamine (Ishikawa reagent), 1,1,2-trifluoro-2-chloroethyl-N,N-dimethylamine or 1,1,2-trifluoro-2-chloroethyl-N,N-diethylamine (Yarovenko reagent). Here, preference is given to 1,1,2,2-tetrafluoroethyl-N,N-dimethylamine and 1,1,2,2-tetrafluoroethyl-N,N-diethylamine, and particular preference is given to 1,1,2,2-tetrafluoroethyl-N,N-dimethylamine.

The acrylic acid hydrazones of the formula (VI) used in step (C) are preferably selected from the group consisting of ethyl (2E)-3-[1-methyl-2-(propan-2-ylidene)hydrazinyl]prop-2-enoate, ethyl (2Z)-3-[1-methyl-2-(propan-2-ylidene)hydrazinyl]prop-2-enoate, methyl 3-[1-methyl-2-(propan-2-ylidene)hydrazinyl]prop-2-enoate, propyl 3-[1-methyl-2-(propan-2-ylidene)-hydrazinyl]prop-2-enoate, ethyl (2E)-3-[1-methyl-2-(3,3-dimethylbutan-2-ylidene)hydrazinyl]prop-2-enoate, methyl 3-[1-methyl-2-(3,3-dimethylbutan-2-ylidene)hydrazinyl]prop-2-enoate, methyl 3-[1-methyl-2-(phenylmethylidene)hydrazinyl]prop-2-enoate, (2E)-3-[1-methyl-2-(phenylmethylidene)hydrazinyl]prop-2-enenitrile and methyl 3-[1-ethyl-2-(propan-2-ylidene)-hydrazinyl]prop-2-enoate.

In a preferred embodiment of the process according to the invention, the α,α-dihaloamine: is initially reacted with a Lewis acid [1L], such as, for example, $BF_3$, $AlCl_3$, $SbCl_5$, $SbF_5$, $ZnCl_2$, $PF_5$, and the mixture of the hydrazinoacrylic ester of the formula (VI) and a base, neat or dissolved in a suitable solvent, is then added.

Preference is given to organic bases such as trialkylamines, alkylpyridines, phosphazenes and 1,8-diazabicyclo[5.4.0]undecene (DBU), alkali metal hydroxides, such as, for example, lithium hydroxide, sodium hydroxide or potassium hydroxide, alkali metal carbonates ($Na_2CO_3$, $K_2CO_3$) and alkoxides, such as, for example, NaOMe, NaOEt, NaOt-Bu, KOt-Bu.

The reaction of the α,α-dihaloamines of the formula (XI) with the acrylic acid hydrazones of the formula (VI) is usually carried out at temperatures of from −50 to 70° C., preferably from −20 to 60° C., particularly preferably from −10 to 50° C.

The reaction can be carried out under reduced pressure, under atmospheric pressure or under elevated pressure and is preferably carried out under atmospheric pressure.

The reaction can be carried out in the absence of a solvent or in a solvent. The reaction is preferably carried out in a solvent. Suitable solvents are, for example, selected from the group consisting of aliphatic and aromatic hydrocarbons, such as, for example, n-hexane, benzene or toluene, which may be substituted by fluorine and chlorine atoms, such as methylene chloride, dichloroethane, fluorobenzene, chlorobenzene or dichlorobenzene; ethers, such as, for example, diethyl ether, diphenyl ether, methyl tert-butyl ether, isopropyl ethyl ether, dioxane, diglym, dimethylglycol, dimethoxyethane (DME) or THF; nitriles, such as methylnitrile, butylnitrile or phenylnitrile; amides, such as dimethylformamide (DMF) or N-methylpyrrolidone (NMP), or mixtures of such solvents, with acetonitrile, dichloromethane, THF, DME and ethyl acetate being particularly preferred.

The base and the acrylic acid hydrazone of the formula (VI) are preferably employed in equimolar amounts, based on the α,α-dihaloamines of the formula (XI). The base can also be used in excess. According to the invention, the ratio of base: hydrazinoacrylic acid derivative is from 1.5:1 to 0.9:1, preferably from 1.4:1, particularly preferably from 1.3:1 to 1.05:1.

Owing to the susceptibility of the α,α-dihaloamines to hydrolysis, the reaction is to be carried out under an atmosphere of inert gas in apparatus free from water.

Possible intermediates which may result in accordance with the present invention from reaction step (C) are usually the hydrazinoaminium salts of the formula (VIIb).

The intermediates formed can be used without prior work-up for the cyclization step (step D).

Alternatively, the intermediates can be isolated by suitable work-up steps and, if appropriate, further purification and can be used at a later point in time for the cyclization (step D).

Step (D): Cyclization

According to the invention, the cyclization of the intermediates obtainable from steps (A), (B) or (C) is carried out at temperatures of from −20° C. to +150° C., preferably at temperatures of from −10° C. to +100° C., particularly preferably at from −10 to 50° C., and under atmospheric pressure.

The reaction time is not critical and can be chosen from a relatively wide range, depending on the batch size.

According to the invention, the ring closure to the pyrazole is carried out in the presence of an acid. Here, the carbonyl compound $R^8R^9C=O$ is cleaved off. The carbonyl compounds can be separated off and recycled into the preparation of hydrazones of the formula (III).

Usually, step (D) is carried out after step (A), (B) or (C) without a change of solvent.

Ideally, all reaction steps of the process according to the invention are carried out in the same solvent.

Suitable solvents are, for example, aliphatic, alicyclic or aromatic hydrocarbons, such as, for example, petroleum ether, n-hexane, n-heptane, cyclohexane, methylcyclohexane, benzene, toluene, xylene or decaline, and halogenated hydrocarbons, such as, for example, chloro-benzene, dichlorobenzene, dichloromethane, chloroform, carbon tetrachloride, dichloroethane or trichloroethane, ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles, such as acetonitrile, propionitrile, n- or isobutyronitrile or benzonitrile; ketones, such as acetone, methyl ethyl ketone, methyl isobutyl ketone or cyclohexanone; amides, such as N,N-dimethylformamide, N,N-dimethylacetamide, N-methylformanilide, N-methylpyrrolidone or hexamethylphosphoric triamide; sulphoxides, such as dimethyl sulphoxide, or sulphones, such as sulpholane; alcohols, such as methanol, ethanol, n- or isopropanol, butanol. Particular preference is given to using toluene, xylene, chlorobenzene, n-hexane, cyclohexane or methylcyclohexane, ethanol, very particularly preferably ethanol, toluene, xylene and water.

Suitable acids are selected from the group consisting of HCl, $H_2SO_4$, $CF_3COOH$, $CF_3SO_3H$, $CH_3COOH$; particular preference is given to HCl and $H_2SO_4$.

After the reaction has ended, for example, the solvents are removed and the product is isolated by filtration or initially extracted with water, the organic phase is separated off and the solvent is removed by distillation.

The process according to the invention is illustrated in more detail by the examples below. However, the examples are not to be interpreted as limiting.

PREPARATION EXAMPLES

Example 1

Ethyl 3-(difluoromethyl)-1-methyl-1H-pyrazole-4-carboxylate

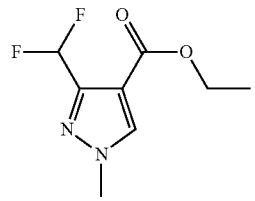

5.8 g (25 mmol) of ethyl 2-(ethoxymethylidene)-4,4-difluoro-3-oxobutanoate are initially charged in 25 ml of acetonitrile, and 2.25 g of (1-methylethylidene)hydrazone are added over a period of 5 min. The mixture is stirred at RT for 1 h, and 0.5 ml of 10% strength HCl is added. GC shows only one isomer. The mixture is concentrated and the product is washed with cold water. Yield 4.83 g (94%).

$^{19}$F-NMR (CDCl$_3$): δ=−117.2 (d) ppm.

$^1$H-NMR (CDCl$_3$): δ=1.35 (t, 3H); 3.96 (s, 3H); 4.31 (kw, 2H); 7.10 (t, 1H), 8.15 (s, 1H) ppm.

Example 2

In a departure from Example 1, methyl 2-(1-methylethylidene)hydrazone is used.

Yield 92%.

Example 3

48.8 g of 1,1,2,2-tetrafluoroethyldimethylamine are initially charged in 500 ml of acetonitrile, and 330 g of BF$_3$ (19% strength solution in CH$_3$CN) are added slowly. Subsequently, 55 g of ethyl 3-[1-methyl-2-(1-methylethylidene)hydrazino] prop-2-enoate are metered in over a period of 15-20 min, and the mixture is stirred at RT for 1.5 h. 1 ml of HCl is added to the mixture, and the acetonitrile is removed under reduced pressure. The light-yellow precipitate formed is washed with water and dried. Yield: 58 g, (94% of theory), m.p. 64-65° C., w.w. % 99%.

Example 4

Ethyl 3-(chlorofluoromethyl)-1-methyl-1H-pyrazole-4-carboxylate

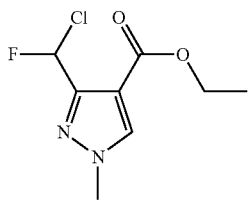

In a departure from Example 1, 2-(ethoxymethylidene)-4-chloro-4-fluoro-3-oxobutanoate is used.
$^{19}$F-NMR (CDCl$_3$): δ=−133.8 (d, J=47.5) ppm.

Example 5

Ethyl 4,4-difluoro-2-{[1-methyl-2-(phenylmethylidene)hydrazino]-methylidene}-3-oxobutanoate

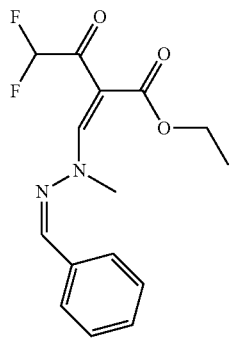 [SMILES: CCOC(=O)/C(=C\N(C)/N=C\c1ccccc1)C(=O)C(F)F]

6.2 g of 2-methyl-1-phenylhydrazone and 9.3 g of ethyl 2-(difluoroacetyl)-3-(dimethyl-amino)acrylate are initially charged in 100 ml of toluene, and 5.7 g of potassium bisulphate are added. The reaction mixture is then heated at 35-40° C. and stirred at the same temperature for 8 h. The salts are separated off, and the solvent is then removed under reduced pressure. This gives ethyl 4,4-difluoro-2-{[1-methyl-2-(phenylmethylidene)hydrazino]methylidene}-3-oxobutanoate as a solid (91% yield). The isomer ratio according to NMR is 53/39%.
$^1$H-NMR (278 K, CDCN$_3$): δ=1.08 (t, 3H); 1.23 (t, 3H); 3.44 (s, 3H); 3.52 (s, 3H); 4.14 (m, 2H); 6.0 (t, 1H); 6.37 (t, 1H); 7.4-7.98 (m, 7H) ppm.

Method for the Reoioselective Synthesis of 1-Alkyl-3-Haloalkyl-Pyrazole-4-Carboxylic Acid Derivatives The present invention relates to a process for the regioselective synthesis of 1-alkyl-3-halo-alkylpyrazole-4-carboxylic acid derivatives by cyclization of 2,3-disubstituted acrylic acid derivatives, and to the hydrazones formed as intermediates in the process.

2-Dihaloacyl-3-dialkylaminoacrylic esters of the formula II (Y═COOAlk, Z═O) are useful intermediates for the preparation of dihalomethyl-substituted pyrazolylcarboxylic acid derivatives which for their part are precursors of fungicidally active compounds (cf. WO 03/070705).

Pyrazolecarboxylic acid derivatives are usually prepared by reacting acrylic acid derivatives having two leaving groups (Z and A) with hydrazines.

The reaction with the monoalkylhydrazines gives mainly 1-alkylpyrazoles. However, the cyclization is frequently not regioselective. As a consequence, depending on the substrate and the reaction conditions, the unwanted 5-alkylpyrazoles are formed in amounts between 10 and 80% (see Scheme 1).

Scheme 1

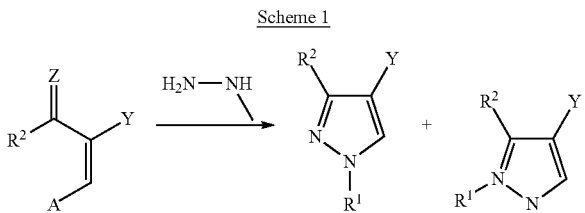

The synthesis of 1-alkylpyrazolecarboxylic acid derivatives by alkylation of pyrazole derivatives unsubstituted in the 1-position frequently also proceeds with formation of both regioisomers (see Scheme 2).

Scheme 2

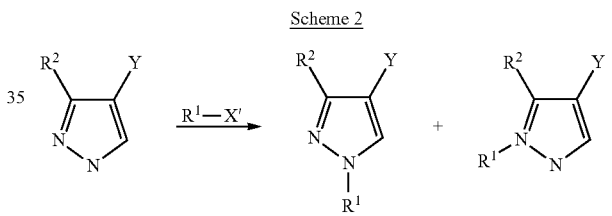

An alternative route of preparing fluorohaloalkylpyrazole-carboxylic acids is the cyclization of, for example, 4,4-dichloro-2-[(dimethylamino)methylidene]-3-oxobutanoate with alkyl-hydrazines followed by a halogen exchange.

WO 2005/042468 discloses a process for preparing 2-dihaloacyl-3-aminoacrylic esters by reacting acid halides with dialkylaminoacrylic esters, followed by their cyclization with alkylhydrazines.

The European patent application No. 07117232.4, hitherto unpublished, describes a process for preparing HCl-free 2-dihaloacyl-3-aminoacrylic esters by reacting acid fluorides with dialkyl-aminoacrylic acid derivatives. The process can be carried out in the absence of a base, as a result of which the removal of halide salts is not required.

WO 2008/092583 describes a process for preparing 3-dihalomethylpyrazole-4-carboxylic acid derivatives by reacting α,α-fluoroamines in the presence of Lewis acids with acrylic acid derivatives, followed by their reaction with alkylhydrazines.

WO 2006/090778 discloses a process for preparing 1-methyl-3-difluoromethylpyrazole-carboxylic esters by cyclization of 2-alkoxymethylenefluoroacylacetate with methylhydrazine in the presence of water and a base.

However, the processes above-described all have the disadvantage that the cyclization, even at low temperatures, proceeds only with unsatisfactory regioselectivity.

In view of the prior art described above, it is an object of the present invention to provide a process which does not have the disadvantages mentioned above, thus providing regioselective access to 1-alkyl-3-haloalkylpyrazole-4-carboxylic acid derivatives.

The object described above was achieved by a process for preparing 1-alkyl-3-haloalkyl-pyrazole-4-carboxylic acid derivatives of the formula (I)

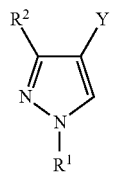

(I)

in which $R^1$ is selected from the group consisting of $C_{1-12}$-alkyl, $C_{3-8}$-cycloalkyl, $C_{2-12}$-alkenyl, $C_{2-12}$-alkynyl, $C_{6-8}$-aryl, $C_{7-19}$-arylalkyl and $C_{7-19}$-alkylaryl groups, each of which may be substituted by one or more groups selected from the group consisting of —R', —X', —OR', —SR', —NR'$_2$, —SiR'$_3$, —COOR', —(C=O)R', —CN and —CONR$_2$', where R' is hydrogen or a $C_{1-12}$-alkyl group;

$R^2$ is selected from $C_1$-$C_4$-alkyl groups which may be substituted by one, two or three halogen atoms selected from the group consisting of F, Cl and Br or by a $CF_3$ group;

Y is selected from the group consisting of (C=O)OR$^3$, CN and (C=O)NR$^4$R', where $R^3$, $R^4$ and $R^5$ independently of one another are selected from the group consisting of $C_{1-12}$-alkyl, $C_{3-8}$-cycloalkyl, $C_{2-12}$-alkenyl, $C_{2-12}$-alkynyl, $C_{6-8}$-aryl, $C_{7-19}$-arylalkyl and $C_{7-19}$-alkylaryl groups, each of which may be substituted by one or more groups selected from the group consisting of —R', —X', —OR', —SR', —NR'$_2$, —SiR'$_3$, —COOR', —(C=O)R', —CN and —CONR$_2$', where R' is hydrogen or a $C_{1-12}$-alkyl group, and $R^4$ and $R^5$ together with the nitrogen atom to which they are attached may form a 5- or 6-membered ring which may optionally contain one or more further heteroatoms selected from the group consisting of O, S and an SO$_2$ group and which may be substituted by one or more groups selected from the group consisting of —R', —X', —OR', —SR', —NR'$_2$, —SiR'$_3$, —COOR', —CN and —CONR$_2$', where R' is hydrogen or a $C_{1-12}$-alkyl group;

comprising at least one of the reaction sequences consisting of steps (A) and (D), (B) and (D) or (C) and (D) below:

(A) reaction of a 2-acylated or 2-iminoalkylated acrylic acid derivative of the formula (II),

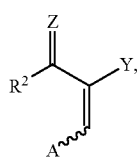

(II)

in which

Z is selected from the group consisting of O, S and N$^+$R$^{10}$R$^{11}$, where $R^{10}$ and $R^{11}$ independently of one another are selected from the group consisting of $C_{1-12}$-alkyl, $C_{3-8}$-cycloalkyl, $C_{2-12}$-alkenyl, $C_{2-12}$-alkynyl, $C_{6-8}$-aryl, $C_{7-19}$-arylalkyl and $C_{7-19}$-alkylaryl groups, each of which may be substituted by one or more groups selected from the group consisting of —R', —X', —OR', —SR', —NR'$_2$, —SiR'$_3$, —COOR', —(C=O)R', —CN and —CONR$_2$', where R' is hydrogen or a $C_{1-12}$-alkyl group, and $R^{10}$ and $R^{11}$ together with the nitrogen atom to which they are attached may form a 5- or 6-membered ring which may optionally contain one or two further heteroatoms selected from the group consisting of O, S and an SO$_2$ group and which may be substituted by one or more groups selected from the group consisting of —R', —X', —OR', —SR', —NR'$_2$, —SiR'$_3$, —COOR', —(C=O)R', —CN and —CONR$_2$', where R' is hydrogen or a $C_{1-12}$-alkyl group;

A is a leaving group selected from the group consisting of OR$^{12}$, SR$^{12}$ and NR$^{12}$R$^{13}$, where $R^{12}$ and $R^{13}$ independently of one another are selected from the group consisting of $C_{1-12}$-alkyl, $C_{3-8}$-cycloalkyl, $C_{2-12}$-alkenyl, $C_{2-12}$-alkynyl, $C_{6-8}$-aryl, $C_{7-19}$-arylalkyl and $C_{7-19}$-alkylaryl groups, each of which may be substituted by one or more groups selected from the group consisting of —R', —X', —OR', —SR', —NR'$_2$, —SiR'$_3$, —COOR', —(C=O)R', —CN and —CONR$_2$', where R' is hydrogen or a $C_{1-12}$-alkyl group, and $R^{12}$ and $R^{13}$ together with the nitrogen atom to which they are attached may form a 5- or 6-membered ring which may optionally contain one or two further heteroatoms selected from the group consisting of O, S and an SO$_2$ group and which may be substituted by one or more groups selected from the group consisting of —R', —X', —OR', —SR', —NR'$_2$, —SiR'$_3$, —COOR', —(C=O)R', —CN and —CONR$_2$', where R' is hydrogen or a $C_{1-12}$-alkyl group;

with an N-alkylhydrazone of the formula (III)

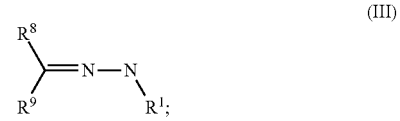

(III)

in which $R^8$ and $R^9$ independently of one another are selected from the group consisting of hydrogen, $C_{1-12}$-alkyl, $C_{3-8}$-cycloalkyl, $C_{2-12}$-alkenyl, $C_{2-12}$-alkynyl, $C_{6-8}$-aryl, $C_{7-19}$-arylalkyl and $C_{7-19}$-alkylaryl groups, each of which may be substituted by one more groups selected from the group consisting of —R', —X', —OR', —SR', —NR'$_2$, —SiR'$_3$, —COOR', —(C=O)R', —CN and —CONR$_2$', where R' is hydrogen or a $C_{1-12}$-alkyl group, and $R^8$ and $R^9$ together with the carbon atom to which they are attached may form a 5- or 6-membered ring which may optionally contain one or two further heteroatoms selected from the group consisting of O, S and an SO$_2$ group and which may be substituted by one or more groups selected from the group consisting of —R', —X', —OR', —SR', —NR'$_2$, —SiR'$_3$, —COOR', —(C=O)R', —CN and —CONR$_2$', where R' is hydrogen or a $C_{1-12}$-alkyl group;

(B) acylation of an acrylic acid hydrazone of the formula (VI);

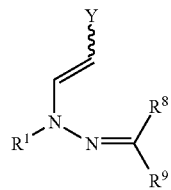

with an acyl halide of the formula (X), where X' is selected from the group consisting of F, Cl, Br and I,

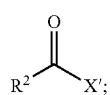

(C) iminoalkylation of an acrylic acid hydrazone of the formula (VI) above with an α,α-dihaloamine of the formula (XI), where X' is selected from the group consisting of F, Cl, Br and I,

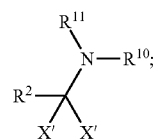

(D) cyclization of the intermediates obtained in step (A), (B) or (C) to give the 3-haloalkylpyrazole-4-carboxylic acid derivative of the formula (I).

Surprisingly, under the conditions according to the invention, the 1-alkyl-3-haloalkyl-pyrazole-4-carboxylic acid derivatives of the formula (I) can be prepared with good yields, regioselectivities and in high purity, the process according to the invention thus overcoming the disadvantages mentioned above of the preparation processes described in the prior art.

GENERAL DEFINITIONS

In the context of the present invention, the term halogens (X') comprises, unless defined otherwise, elements selected from the group consisting of fluorine, chlorine, bromine and iodine, where fluorine, chlorine and bromine are used with preference and fluorine and chlorine with particular preference.

Optionally substituted groups may be mono- or polysubstituted where in the case of polysubstitution the substituents may be identical or different.

Alkyl groups substituted by one or more halogen atoms (—X') are, for example, selected from the group consisting of trifluoromethyl ($CF_3$), difluoromethyl ($CHF_2$), $CF_3CH_2$, $ClCH_2$, $CF_3CCl_2$.

In the context of the present invention, unless defined otherwise, alkyl groups are straight-chain or branched hydrocarbon groups which may optionally have one, two or more heteroatoms selected from the group consisting of O, N, P and S. Moreover, the alkyl groups according to the invention may optionally be substituted by further groups selected from the group consisting of —R', halogen (—X'), alkoxy (—OR'), thioether or mercapto (—SR'), amino (—NR'$_2$), silyl (—SiR'$_3$), carboxyl (—COOR'), cyano (—CN), acyl (—(C=O)R') and amide (—CONR$_2$') groups, where R' is hydrogen or a $C_{1-12}$-alkyl group, preferably a $C_{2-10}$-alkyl group, particularly preferably a $C_{3-8}$alkyl group, which may have one or more heteroatoms selected from the group consisting of N, O, P and S.

In the context of the present invention, cycloalkyl groups are, unless defined otherwise, monocyclic saturated hydrocarbon groups having 3 to 8 carbon ring members, which groups may optionally contain one, two or more heteroatoms selected from the group consisting of O, N, P and S. Moreover, the cycloalkyl groups according to the invention may optionally be substituted by further groups selected from the group consisting of —R', halogen (—X'), alkoxy (—OR'), thioether or mercapto (—SR'), amino-(—NR'$_2$), silyl (—SiR'$_3$), carboxyl (—COOR'), cyano (—CN), acyl (—(C=O)R') and amide (—CONR$_2$') groups, where R' is hydrogen or a $C_{1-12}$-alkyl group, preferably a $C_{2-10}$-alkyl group, particularly preferably a $C_{3-8}$-alkyl group, which may contain one or more heteroatoms selected from the group consisting of N, O, P and S.

Specifically, this definition comprises, for example, the meanings cyclopropyl, cyclobutyl, cyclopentyl and cyclohexyl.

The definition $C_1$-$C_{12}$-alkyl comprises the largest range defined herein for an alkyl group. Specifically, this definition comprises, for example, the meanings methyl, ethyl, n-, isopropyl, n-, iso-, sec- and t-butyl, n-pentyl, n-hexyl, 1,3-dimethylbutyl, 3,3-dimethylbutyl, n-heptyl, n-nonyl, n-decyl, n-undecyl, n-dodecyl.

In the context of the present invention, alkenyl groups are, unless defined otherwise, straight-chain or branched hydrocarbon groups which contain at least one single unsaturation (double bond) and may optionally have one, two or more single or double unsaturations or one, two or more heteroatoms selected from the group consisting of O, N, P and S. Moreover, the alkenyl groups according to the invention may optionally be substituted by further groups selected from the group consisting of —R', halogen (—X'), alkoxy (—OR'), thioether or mercapto (—SR'), amino (—NR'$_2$), silyl (—SiR'$_3$), carboxyl (—COOR'), cyano (—CN), acyl (—(C=O)R') and amide (—CONR$_2$') groups, where R' is hydrogen or a $C_{1-12}$-alkyl group, preferably a $C_{2-10}$-alkyl group, particularly preferably a $C_{3-8}$-alkyl group, which may contain one or more heteroatoms selected from the group consisting of N, O, P and S.

The definition $C_2$-$C_{12}$-alkenyl comprises the largest range defined herein for an alkenyl group. Specifically, this definition comprises, for example, the meanings vinyl; allyl (2-propenyl), isopropenyl (1-methylethenyl); but-1-enyl(crotyl), but-2-enyl, but-3-enyl; hex-1-enyl, hex-2-enyl, hex-3-enyl, hex-1-enyl, hex-5-enyl; hept-1-enyl, hept-2-enyl, hept-3-enyl, hept-4-enyl, hept-5-enyl, hept-6-enyl; oct-1-enyl, oct-2-enyl, oct-3-enyl, oat-4-enyl, oct-5-enyl, oct-6-enyl, oct-7-enyl; non-2-enyl, non-3-enyl, non-4-enyl, non-6-enyl, non-7-enyl, non-8-enyl; dec-1-enyl, dec-2,-enyl; dec-3-enyl, dec-4-enyl, dec-5-enyl, dec-6-enyl, dec-7-enyl, dec-8-enyl, dec-9-enyl; undec-1-enyl, under-2-enyl, undec-3-enyl, undec-4-enyl, undec-5-enyl, undec-6-enyl, undec-7-enyl, undec-8-enyl, undec-9-enyl, undec-10-enyl; dodec-1-enyl, dodec-2-enyl, dodec-3-enyl, dodec-4-enyl, dodec-5-enyl, dodec-6-enyl, dodec-7-enyl, dodec-8-enyl, dodec-9-enyl, dodec-10-enyl, dodec-11-enyl; buta-1,3-dienyl, penta-1,3-dienyl.

In the context of the present invention, cycloalkenyl groups are, unless defined otherwise, monocyclic nonaromatic hydrocarbon groups having 3 to 8 carbon ring members and at least one double bond, which groups may optionally contain one, two or more heteroatoms selected from the group consisting of O, N, P and S. Moreover, the cycloalkenyl groups according to the invention may optionally be substituted by further groups selected from the group consisting of —R', halogen (—X'), alkoxy (—OR'), thioether or mercapto (—SR'), amino (—NR'$_2$), silyl (—SiR'$_3$), carboxyl (—COOR'), cyano (—CN), acyl (—(C=O)R') and amide (—CONR$_2$') groups, where R' is hydrogen or a $C_{1-12}$-alkyl group, preferably a $C_{2-10}$-alkyl group, particularly preferably a $C_{3-8}$-alkyl group, which may contain one or more heteroatoms selected from the group consisting of N, O, P and S.

Specifically, this definition comprises, for example, the meanings cyclopenten-1-yl, cyclohexen-1-yl, cyclohepta-1,3-dien-1-yl.

In the context of the present invention, alkynyl groups are, unless defined otherwise, straight-chain, branched or cyclic hydrocarbon groups which contain at least one double unsaturation (triple bond) and may optionally have one, two or more single or double unsaturations or one, two or more heteroatoms selected from the group consisting of O, N, P and S. Moreover, the alkynyl groups according to the invention may optionally be substituted by further groups selected from the group consisting of —R', halogen (—X'), alkoxy (—OR'), thioether or mercapto (—SR'), amino (—NR'$_2$), silyl (—SiR'$_3$), carboxyl (—COOR'), cyano (—CN), acyl (—(C=O)R') and amide (—CONR$_2$') groups, where R' is hydrogen or a straight-chain, branched or cyclic $C_{1-12}$-alkyl group which may contain one or more heteroatoms selected from the group consisting of N, O, P and S.

The definition $C_2$-$C_{12}$-alkynyl comprises the largest range defined herein for an alkynyl group. Specifically, this definition comprises, for example, the meanings ethynyl(acetylenyl); prop-1-inyl and prop-2-inyl.

In the context of the present invention, aryl groups are, unless defined otherwise, aromatic hydrocarbon groups which may contain one, two or more heteroatoms selected from the group consisting of O, N, P and S and which may optionally be substituted by further groups selected from the group consisting of —R', halogen (—X'), alkoxy (—OR'), thioether or mercapto (—SR'), amino (—NR'$_2$), silyl (—SiR'$_3$), carboxyl (—COOR'), cyano (—CN), acyl (—(C=O)R') and amide (—CONR$_2$') groups, where R' is hydrogen or a $C_{1-12}$-alkyl group, preferably a $C_{2-10}$-alkyl group, particularly preferably a $C_{3-8}$-alkyl group, whicl may contain one or more heteroatoms, selected from the group consisting of N, O, P and S.

The definition $C_{5-18}$-aryl comprises the largest range defined herein for an aryl groups having 5 to 18 skeleton atoms, where the carbon atoms may be replaced by heteroatoms. Specifically, this definition comprises, for example, the meanings cyclopentadienyl, phenyl, cyclohepta-trienyl, cyclooctatetraenyl, naphthyl and anthracenyl; 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl; 1-pyrrolyl, 1-pyrazolyl, 1,2,4-triazol-1-yl, 1-imidazolyl, 1,2,3-triazol-1-yl, 1,3,4-triazol-1-yl; 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

In the context of the present invention, arylalkyl groups (aralkyl groups) are, unless defined otherwise, alkyl groups which are substituted by aryl groups, which may have a $C_{1-8}$-alkylene chain and which may be substituted in the aryl skeleton or the alkylene chain by one or more heteroatoms selected from the group consisting of O, N, P and S and optionally by further groups selected from the group consisting of —R', halogen-(—X'), alkoxy (—OR'), thioether or mercapto (—SR'), amino (—NR'$_2$), silyl (—SiR'$_3$), carboxyl (—COOR'), cyano (—CN), acyl (—(C=O)R') and amide (—CONR$_2$') groups, where R' is hydrogen or a $C_{1-12}$-alkyl group, preferably a $C_{2-10}$-alkyl group, particularly preferably a $C_{3-8}$-alkyl group, which may contain one or more heteroatoms selected from the group consisting of N, O, P and S.

The definition $C_{7-19}$-aralkyl group comprises the largest range defined herein for an arylalkyl group having a total of 7 to 19 atoms in the skeleton and the alkylene chain. Specifically, this definition comprises, for example, the meanings benzyl and phenylethyl.

In the context of the present invention, alkylaryl groups (alkaryl groups) are, unless defined otherwise, aryl groups which are substituted by alkyl groups, which may have a $C_{1-8}$-alkylene chain and which may be substituted in the aryl skeleton or the alkylene chain by one or more heteroatoms selected from the groups consisting of O, N, P and S and optionally by further groups selected from the group consisting of —R', halogen (—X'), alkoxy (—OR'), thioether or mercapto (—SR'), amino (—NR'$_2$), silyl (—SiR'$_3$), carboxyl (—COOR'), cyano (—CN), acyl (—(C=O)R') and amide (—CONR$_2$') groups, where R' is hydrogen or a $C_{1-12}$-alkyl group, preferably a $C_{2-10}$-alkyl group, particularly preferably a $C_{3-8}$-alkyl group, which may contain one or more heteroatoms selected from the group consisting of N, O, P and S.

The definition $C_{7-19}$-alkylaryl group comprises the largest range defined herein for an alkylaryl group having a total of 7 to 19 atoms in the skeleton and the alkylene chain. Specifically, this definition comprises, for example, the meanings tolyl, 2,3-, 2,4-, 2,5-, 2,6-, 3,4- or 3,5-dimethylphenyl.

The alkyl, alkenyl, alkynyl, aryl, alkaryl and aralkyl groups may furthermore contain one or more heteroatoms which—unless defined otherwise—are selected from the group consisting of N, O, P and S. Here, the heteroatoms replace the carbon atoms specified.

If appropriate, the compounds according to the invention can be present as mixtures of various possible isomeric forms, in particular of stereoisomers, such as, for example, E and Z, threo and erythro and also optical isomers, and, if appropriate, also of tautomers. What is disclosed and claimed are both the E and the Z isomers, and also the threo and erythro isomers and the optical isomers, any mixtures of these isomers, and also the possible tautomeric forms.

Scheme 3 below summarizes the individual variants of the process according to the invention:

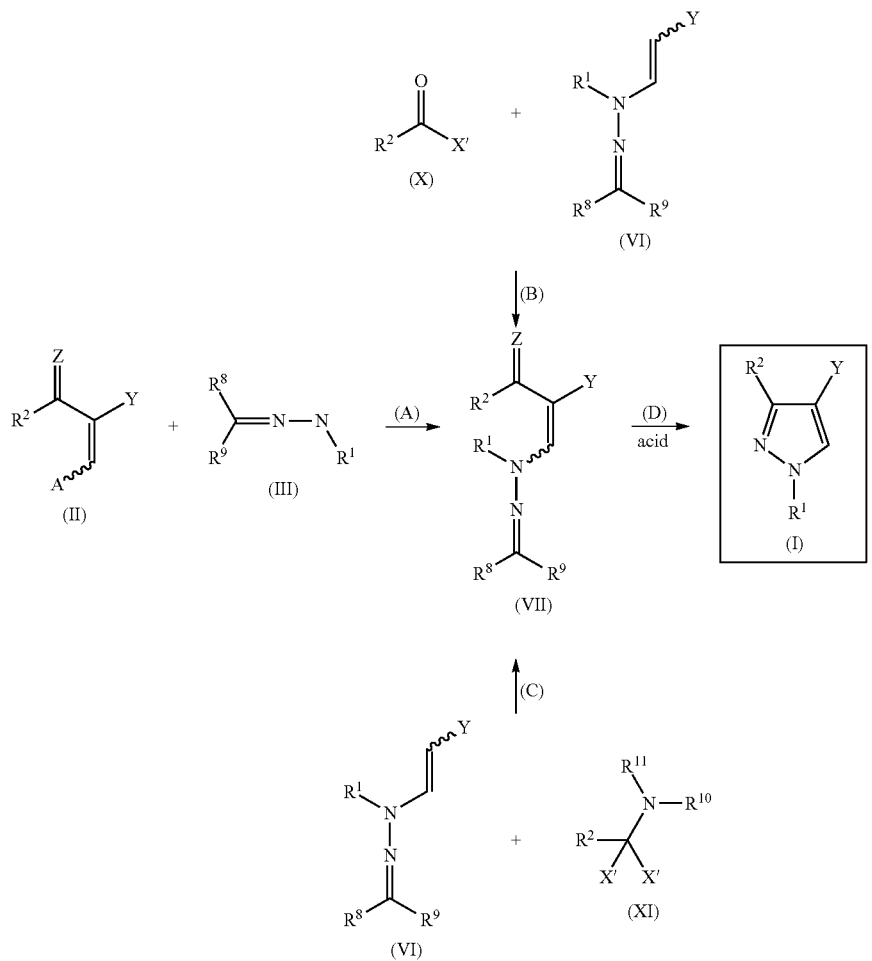

The 1-alkyl-3-haloalkylpyrazole-4-carboxylic acid derivatives obtainable by the process according to the invention are compounds of the formula (I)

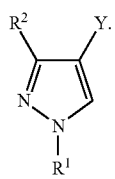

According to the invention, the radicals in formula (I) have the meanings below.

$R^1$ is selected from the group consisting of $C_{1-12}$-alkyl, $C_{3-8}$-cycloalkyl, $C_{2-12}$-alkenyl, $C_{2-12}$-alkynyl, $C_{6-8}$-aryl, $C_{7-19}$-arylalkyl and $C_{7-19}$-alkylaryl groups, each of which may be substituted by one or more groups selected from the group consisting of —R', —X', —OR', —SR', —NR'$_2$, —SiR'$_3$, —COOR', —(C=O)R', —CN and —CONR$_2$', where R' is hydrogen or a $C_{1-12}$-alkyl group;

$R^2$ is selected from $C_1$-$C_4$-alkyl groups which may be substituted by one, two or three halogen atoms selected from the group consisting of F, Cl and Br or by a $CF_3$ group;

Y is selected from the group consisting of (C=O)OR$^3$, CN and (C=O)NR$^6$R$^5$, where R$^3$ and R$^5$ independently of one another are selected from the group consisting of $C_{1-12}$-alkyl, $C_{3-8}$-cycloalkyl, $C_{3-12}$-alkenyl, $C_{2-12}$-alkynyl, $C_{6-8}$-aryl, $C_{7-19}$-arylalkyl and $C_{7-19}$-alkylaryl groups, each of which may be substituted by one or more groups selected from the group consisting of —R', —X', —OR', —SR', —NR'$_2$, —SiR'$_3$, —COOR', —(C=O)R', —CN and —CONR$_2$', where R' is hydrogen or a $C_{1-12}$-alkyl group, and R$^4$ and R$^5$ together with the nitrogen atom to which they are attached may form a 5- or 6-membered ring which may optionally contain one or more further heteroatoms selected from the group consisting of O, S and an SO$_2$ group and which may be substituted by one or more groups selected from the group consisting of —R', —X', —OR', —SR', —NR'$_2$, —SiR'$_3$, —COOR', —(C=O)R', —CN and —CONR$_2$', where R' is hydrogen or a $C_{1-12}$-alkyl group.

In a preferred embodiment of the present invention, the radicals in formula (I) have the meanings below:

$R^1$ is selected from the group consisting of methyl, ethyl, n-propyl and isopropyl, $R^2$ is selected from the group consisting of chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2-difluoroethyl, 2,2-dichloro-2-fluoroethyl, 2,2,2-trichloroethyl, pentafluoroethyl and 1,1,1-trifluoroprop-2-yl; 1,2,2,2-tetrafluoroethyl, Y is selected from the group consisting of (C=O)OR$^3$, CN and (C=O)NR$^4$R$^5$, whew R$^3$, R$^4$ and R$^5$ independently of one another are selected from the group consisting of methyl, ethyl, n-propyl and isopropyl.

In a particularly preferred embodiment of the present invention, the radicals in formula (I) have the meanings below:

$R^1$ is methyl, $R^2$ is selected from the group consisting of trifluoromethyl and difluoromethyl, is selected from the group consisting of (C=O)OR$^3$, where R$^3$ is methyl or ethyl.

Step (A)

In a first embodiment of the present process, which is the result of combining reaction steps (A) and (D), initially 2-acylated or 2-iminoalkylated acrylic acid derivatives of the formula (II) are reacted with N-alkylhydrazones of the formula (III) (Scheme 4). Subsequently, the intermediates formed in step (A) are cyclized to give the 3-haloalkylpyrazole-4-carboxylic acid derivatives of the formula (I) (Step D).

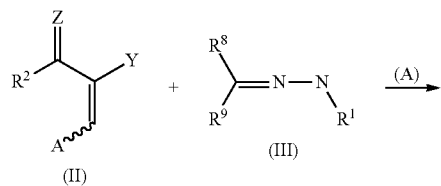

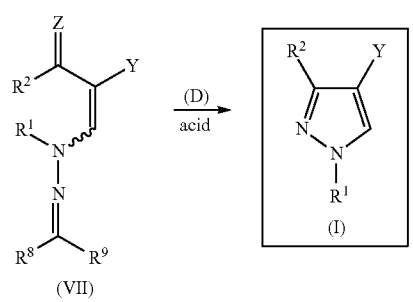

Scheme 4

Possible intermediates which may, in accordance with the present invention, result from reaction step (A) are the acrylhydrazones of the formula (VII)

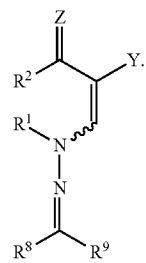

This formula includes in particular the 2-acylhydrazinoprop-2-enoates of the formula (VIIa) and the hydrazinoaminium salts of the formulaa (VIIb)

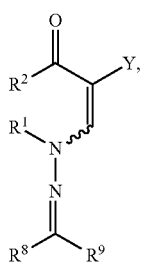

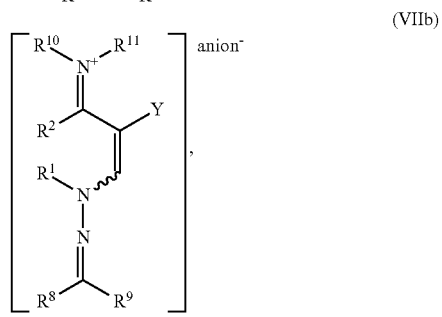

in which the radicals $R^1$, $R^2$, $R^8$ to $R^{11}$ and Y have the meanings described above and which optionally have a counterion (anion$^-$) selected from the group consisting of Cl$^-$, BF$_4^-$, FF$_6^-$, SbF$_6^-$ and AlCl$_4^-$.

The process step (A) according to the invention is preferably carried out in a temperature range of from −20° C. to +150° C., particularly preferably at temperatures of from −10° C. to +70° C.

The process step (A) according to the invention is generally carried out under atmospheric pressure. However, alternatively, it is also possible to operate under reduced pressure to remove the highly volatile dialkylamines.

The reaction time is not critical and may, depending on the batch size and the temperature, be chosen from a range of between a few minutes and a number of hours.

When carrying out the process step (A) according to the invention, 1 mol of the acrylic acid derivative of the formula (II) is reacted with from 0.5 mol to 3 mol, preferably from 0.5 mol to 1.5 mol, particularly preferably with an equimolar amount, of the hydrazone of the formula (III).

Preferably, the hydrazone of the formula (III), dissolved in the solvent, is initially charged, and the acrylic acid derivative of the formula (II) is added. However, it is also possible to reverse the order.

The reaction can be promoted by adding catalysts, such as, for example, $CH_3COOH$, $H_2SO_4$, $KHSO_4$, $NaH_2PO_4$, HCl, $CF_3COOH$, $CH_3COONa$.

Work-up and isolation of the intermediates is generally not required, and the reaction mixture obtainable from step (A) can be used immediately or after storage for the cyclization step (D).

The acrylic acid derivatives of the formula (II) can be obtained by the processes described above, in connection with the prior art.

In the context of the present invention, preference is given to using 2-acylated or 2-iminoalkylated acrylic acid derivatives of the formula (II) selected from the group consisting of ethyl (2-ethoxymethylene)-4,4-difluoromethylacetoacetate, ethyl-(2-ethoxymethylene)-4,4,4-trifluoromethylacetonitrile, 2-[(dimethylamino)methylidene]-4,4,4-trifluoro-3-oxobutanenitrile, N-1-(trifluoromethyl)-3-(dimethylamino)-2-(ethoxycarbonyl)prop-2-en-1-ylidene]-N-methyl-methanaminium chloride, ethyl 2-(difluoroacetyl)-3-(dimethylamino)acrylate, N-1-(difluoromethyl)-3-(dimethylamino)-2-(ethoxycarbonyl)prop-2-en-1-ylidene]-N-methyl-methanaminium tetrafluoroborate and N-[3-(dimethylamino)-2-(ethoxycarbonyl)-1-(1,1,2,2-tetrafluoroethyl)prop-2-en-1-ylidene]-N-methylmethanaminium chloride.

In the context of the present invention, the N-alkylhydrazones of the formula (III) are preferably selected from the group consisting of 1-methyl-2-(1-methylethylidene)hydrazine, 1-methyl-2-(1,2,2-trimethylpropylidene)hydrazine, 1-methyl-2-(1-methylpropylidene)hydrazine, 1-cyclo-hexylidene-2-methylhydrazine, 1-methyl-2-(phenylmethylidene)hydrazine, 1-methyl-2-(1-phenylethylidene)hydrazine, 1-(diphenylmethylidene)-2-methylhydrazine en ethyl-2[(dimethylamino)methylidene]-4,44-trifluoro-3-oxo-butanoat.

The N-alkylhydrazones of the formula (III) have been described in the literature (Zhurnal Organicheskoi Khimii (1968), 4(6), 986-92.) and can be obtained by reacting commercially available hydrazines of the formula (VIII) with carbonyl compounds of the formula (IX) (see Scheme 5).

Scheme 5

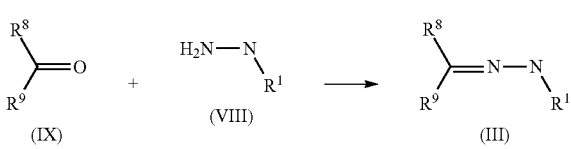

According to the invention, the radicals in formulae (III), (VIII) and (IX) have the meanings below:

$R^1$ is selected from the group consisting of $C_{1-12}$-alkyl, $C_{3-8}$-cycloalkyl, $C_{2-12}$-alkenyl, $C_{2-12}$-alkynyl, $C_{6-8}$-aryl, $C_{7-19}$-arylalkyl and $C_{7-19}$-alkylaryl groups, each of which may be substituted by one or more groups selected from the group consisting of —R', —X', —OR', —SR', —NR'$_2$, —SiR'$_3$, —COOR', —(C=O)R', —CN and CONR$_2$', where R' is hydrogen or a $C_{1-12}$-alkyl group;

$R^8$ and $R^9$ independently of one another are selected from the group consisting of hydrogen, $C_{1-12}$-alkyl, $C_{3-8}$-cycloalkyl, $C_{2-12}$-alkenyl, $C_{2-12}$-alkynyl, $C_{6-8}$-aryl, $C_{7-19}$-arylalkyl and $C_{7-19}$-alkylaryl groups, each of which may be substituted by one more groups selected from the group consisting of —R', —X', —OR', —SR', —NR'$_2$, —SiR'$_3$, —COOR', —(C=O)R', —CN and —CONR$_2$', where R' is hydrogen or a $C_{1-12}$-alkyl group, and $R^8$ and $R^9$ together with the carbon atom to which they are attached may form a 5- or 6-membered ring which may optionally contain one or two further heteroatoms selected from the group consisting of O, S and an $SO_2$ group and which may be substituted by one ot more groups selected from the group consisting of —R', —X', —OR', —SR', —NR'$_2$, —SiR'$_3$, —COOR', —(C=O)R', —CN and —CONR$_2$', where R' is hydrogen or a $C_{1-12}$-alkyl group.

According to the invention, the radicals in formulae (III), (VIII) and (IX) have the preferred meanings below:

$R^1$ is methyl, ethyl, n-propyl, isopropyl, n-butyl, sec-butyl, tert-butyl;

$R^8$ is selected from the group consisting of H, methyl, ethyl, n-propyl, isopropyl, n-butyl, sec-butyl, tert-butyl, phenyl, tolyl, cyclohexyl;

$R^9$ is selected from the group consisting of H, methyl, ethyl, n-propyl, isopropyl, n-butyl, sec-butyl, tert-butyl, phenyl, tolyl, cyclohexyl.

Alternatively, $R^8$ and $R^9$ together with the carbon atom to which they are attached may form a 5- or 6-membered ring.

According to the invention, the radicals in formulae (III), (VIII) and (IX) have the following particularly preferred meanings:

$R^1$ is methyl;

$R^8$ is selected from the group consisting of H, methyl, tert-butyl, phenyl;

$R^9$ is selected from the group consisting of H, methyl, tert-butyl, phenyl.

According to the invention, preference is given to using ketones of the formula (IX) selected from the group consisting of acetone, benzophenone, pinacolone, cyclohexanone, benzaldehyde, with acetone and benzaldehyde being particularly preferably used.

A further advantage of the process according to the invention is the fact that, to prepare the N-methylhydrazones of the formula (III), it is possible to use aqueous methylhydrazine solutions and the explosive concentrated methylhydrazine, which is also used as rocket fuel, is not necessarily required.

In two further embodiments of the process according to the invention which result when the reactions steps (B) and (D) or (C) and (D) are combined, acrylic acid derivatives of the formula (VI) are acylated (step (B)) or iminoalkylated (step (C)) and finally cyclized to give the 3-halo-alkylpyrazole-4-carboxylic acid derivatives of the formula (I) (step D).

Step (B): Acylation

In one embodiment of the process according to the invention, the acrylic acid hydrazones of the formula (VI) are acylated with haloalkylcarbonyl halides of the formula (X) according to Scheme 6 below to give the 2-acylacrylic acid hydrazones of the formula (VIIa). In formula (X), $R^2$ has the above meanings and X' is a halogen atom selected from the group consisting of F, Cl or Br, preferably from the group consisting of F and Cl, particularly preferably F.

In the context of the present invention, the acylating agent used is preferably a haloalkylcarbonyl halide of the formula (X) selected from the group consisting of difluoroacetyl chloride, difluoroacetic anhydride, difluoroacetyl fluoride, trifluoroacetyl chloride and trifluoroacetyl fluoride.

The acrylic acid hydrazones of the formula (VI) used in step (B) are preferably selected from the group consisting of ethyl (2E)-3-[1-methyl-2-(propan-2-ylidene)hydrazinyl] prop-2-enoate, ethyl (2Z)-3-[1-methyl-2-(propan-2-ylidene) hydrazinyl]prop-2-enoate, methyl 3-[1-methyl-2-(propan-2-ylidene)hydrazinyl]prop-2-enoate, propyl 3-[1-methyl-2-(propan-2-ylidene)-hydrazinyl]prop-2-enoate, ethyl (2E)-3-[1-methyl-2-(3,3-dimethylbutan-2-ylidene)hydrazinyl]-prop-2-enoate, methyl 3-[1-methyl-2-(3,3-dimethylbutan-2-ylidene)hydrazinyl]prop-2-enoate, methyl 3-[1'-methyl-2-(phenylmethylidene)hydrazinyl]prop-2-enoate, (2E)-3-[1- methyl-2-(phenylmethylidene)hydrazinyl]prop-2-enenitrile and methyl 3-[1-ethyl-2-(propan-2-ylidene)-hydrazinyl]prop-2-enoate.

Scheme 6

Step (B)

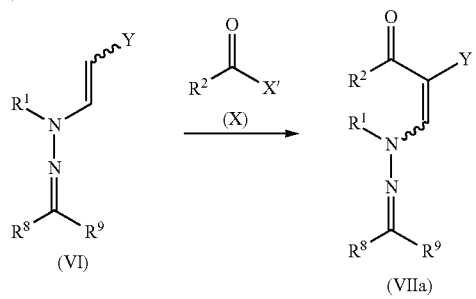

According to the invention, the acylation is carried out at temperatures of from −20° C. to +150° C., preferably at temperatures of from −20° C. to +100° C., particularly preferably at from −10 to 50° C., and under atmospheric pressure.

The reaction time is not critical and may, depending on the batch size and the temperature, be chosen from a range between a few minutes and a number of hours.

According to the invention, 1 mol of the acrylic acid hydrazone of the formula (VI) is reacted with from 0.5 mol to 3 mol, preferably from 1.2 mol to 1.5 mol, particularly preferably with equimolar amounts, of the haloalkylcarbonyl halide of the formula (X).

Preferably, the hydrazinoacrylic acid derivative of the formula (VI) dissolved in the solvent is initially charged, and the haloalkylcarbonyl halide of the formula (X) is added. However, a reverse order is also possible.

The acylation is preferably carried out in the presence of a base. Preference is given here to organic bases, such as trialkylamines, alkylpyridines, phosphazenes and 1,8-diazabicyclo[5.4.0]undecene (DBU); alkali metal hydroxides, such as, for example, lithium hydroxide, sodium hydroxide or potassium hydroxide, alkali metal carbonates ($Na_2CO_3$, $K_2CO_3$) and alkoxides, such as, for example, NaOMe, NaOEt, NaOt-Bu, KOt-Bu.

Suitable solvents are, for example, aliphatic, alicyclic or aromatic hydrocarbons, such as, for example, petroleum ether, n-hexane, n-heptane, cyclohexane, methylcyclohexane, benzene, toluene, xylene or decaline, and halogenated hydrocarbons, such as, for example, chloro-benzene, dichlorobenzene, dichloromethane, chloroform, carbon tetrachloride, dichloroethane or trichloroethane, ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles, such as acetonitrile, propionitrile, n- or isobutyronitrile or benzonitrile; ketones, such as acetone, methyl ethyl ketone, methyl isoburyl ketone or cyclohexanone; amides, such as N,N-dimethylformamide, N,N-dimethylacetamide, N-methylformanilide, N-methylpyrrolidone or hexamethylphosphoric triamide; sulphoxides, such as dimethyl sulphoxide, or sulphones, such as sulpholane. Particular preference is given to using toluene, xylene, chlorobenzene, n-hexane, cyclohexane or methylcyclohexane, very particularly preferably toluene or xylene.

Possible intermediates which, according to the present invention, may result from reaction step (B) are, usually, the 2-acylhydrazinoacrylic acid derivatives of the formula (VIIa).

The intermediates formed can, without prior work-up, be used for the cyclization step (step D).

Alternatively, the intermediates can be isolated by suitable work-up steps and, if appropriate, further purification, and they can be used at a later point in time for the cyclization (step D).

The acrylic acid hydrazones of the formula (VI) have been described in the literature (see Chem. Ber. 1975, 108 (7), 2161-2170; Bulletin de la Societe Chimique de France (1976), (1-2, Pt. 2), 260-4), an d they can be prepared according to Scheme 7 or 8 below.

Scheme 7

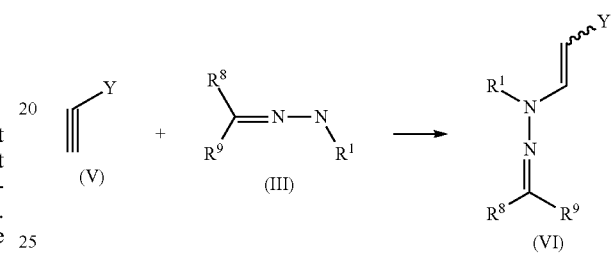

Scheme 8

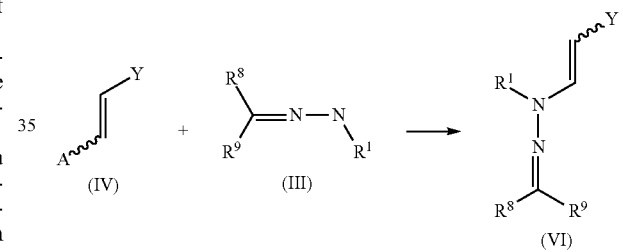

Step (C) Iminoalkylation

In a further embodiment of the process according to the invention, the acrylic acid hydrazones of the formula (VI) are iminoalkylated with at least one α,α-dihaloamine of the formula (XI), according to Scheme 9 below to give the hydrazinoaminium salts of the formula (VIIb). In formula (XI), X' and $R^2$ have the above meanings.

Scheme 9

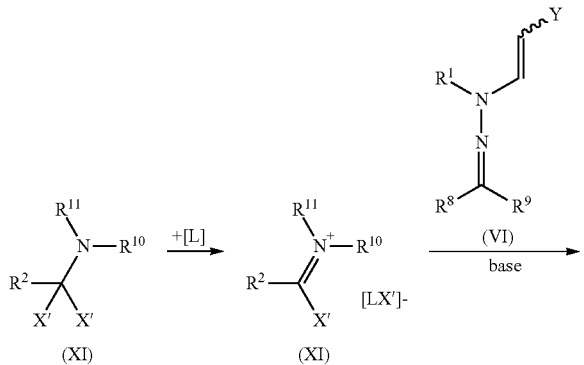

-continued

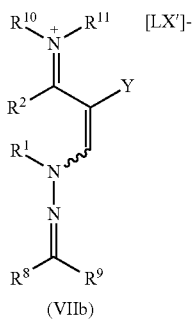

(VIIb)

In Scheme 9 [L] is a Lewis acid.

In the context of the present invention, the iminoalkylating agent of the formula (XI) used may be 1,1,2,2-tetrafluoroethyl-N,N-dimethylamine, 1,1,2,2-tetrafluoroethyl-N,N-diethylamine, 1,1,2-trifluoro-2-(trifluoromethyl)ethyl-N,N-dimethylamine, 1,1,2-trifluoro-2-(trifluoromethyl)-ethyl-N,N-diethylamine (Ishikawa reagent), 1,1,2-trifluoro-2-chloroethyl-N,N-dimethylamine or 1,1,2-trifluoro-2-chloroethyl-N,N-diethylamine (Yarovenko reagent). Here, preference is given to 1,1,2,2-tetrafluoroethyl-N,N-dimethylamine and 1,1,2,2-tetrafluoroethyl-N,N-diethylamine, and particular preference is given to 1,1,2,2-tetrafluoroethyl-N,N-dimethylamine.

The acrylic acid hydrazones of the formula (VI) used in step (C) are preferably selected from the group consisting of ethyl (2E)-3-[1-methyl-2-(propan-2-ylidene)hydrazinyl] prop-2-enoate, ethyl (2Z)-3-[1-methyl-2-(propan-2-ylidene) hydrazinyl]prop-2-enoate, methyl 3-[1-methyl-2-(propan-2-ylidene)hydrazinyl]prop-2-enoate, propyl 3-[1-methyl-2-(propan-2-ylidene)-hydrazinyl]prop-2-enoate, ethyl (2E)-3-[1'-methyl-2-(3,3-dimethylbutan-2-ylidene)hydrazinyl]-prop-2-enoate, methyl 3-[1-methyl-2-(3,3-dimethylbutan-2-ylidene)hydrazinyl]prop-2-enoate, methyl 3-[1-methyl-2-(phenylmethylidene)hydrazinyl]prop-2-enoate, (2E)-3-[1-methyl-2-(phenylmethyl idene)hydrazinyl]prop-2-enenitrile and methyl 3-[1-ethyl-2-(propan-2-ylidene)-hydrazinyl] prop-2-enoate.

In a preferred embodiment of the process according to the invention, the α,α-dihaloamine is initially reacted with a Lewis acid [L], such as, for example, BF$_3$, AlCl$_3$, SbCl$_5$, SbF$_5$, ZnCl$_2$, PF$_5$, and the mixture of the hydrazinoacrylic ester of the formula (VI) and a base, neat or dissolved in a suitable solvent, is then added.

Preference is given to organic bases such as trialkylamines, alkylpyridines, phosphazenes and 1,8-diazabicyclo[5.4.0] undecene (DBU), alkali metal hydroxides, such as, for example, lithium hydroxide, sodium hydroxide or potassium hydroxide, alkali metal carbonates (Na$_2$CO$_3$, K$_2$CO$_3$) and alkoxides, such as, for example, NaOMe, NaOEt, NaOt-Bu, KOt-Bu.

The reaction of the α,α-dihaloamines of the formula (XI) with the acrylic acid hydrazones of the formula (VI) is usually carried out at temperatures of from −50 to 70° C., preferably from −20 to 60° C., particularly preferably from −10 to 50° C.

The reaction can be carried out under reduced pressure, under atmospheric pressure or under elevated pressure and is preferably carried out under atmospheric pressure.

The reaction can be carried out in the absence of a solvent or in a solvent. The reaction is preferably carried out in a solvent. Suitable solvents are, for example, selected from the group consisting of aliphatic and aromatic hydrocarbons, such as, for example, n-hexane, benzene or toluene, which may be substituted by fluorine and chlorine atoms, such as methylene chloride, dichloroethane, fluorobenzene, chlorobenzene or dichlorobenzene; ethers, such as, for example, diethyl ether, diphenyl ether, methyl tert-butyl ether, isopropyl ethyl ether, dioxane, diglym, dimethylglycol, dimethoxyethane (DME) or THF; nitriles, such as methylnitrile, butylnitrile or phenylnitrile; amides, such as dimethylformamide (DMF) or N-methylpyrrolidone (NMP), or mixtures of such solvents, with acetonitrile, dichloromethane, THF, DME and ethyl acetate being particularly preferred.

The base and the acrylic acid hydrazone of the formula (VI) are preferably employed in equimolar amounts, based on the α,α-dihaloamines of the formula (XI). The base can also be used in excess. According to the invention, the ratio of base: hydrazinoacrylic acid derivative is from 1.5:1 to 0.9:1, preferably from 1.4:1, particularly preferably from 1.3:1 to 1.05:1.

Owing to the susceptibility of the α,α-dihaloamines to hydrolysis, the reaction is to be carried out under an atmosphere of inert gas in apparatus free from water.

Possible intermediates which may result in accordance with the present invention from reaction step (C) are usually the hydrazinoaminium salts of the formula (VIIb).

The intermediates formed can be used without prior work-up for the cyclization step (step D).

Alternatively, the intermediates can be isolated by suitable work-up steps and, if appropriate, further purification and can be used at a later point in time for the cyclization (step D).

Step (D): Cyclization

According to the invention, the cyclization of the intermediates obtainable from steps (A), (B) or (C) is carried out at temperatures of from −20° C. to +150° C., preferably at temperatures of from −10° C. to +100° C., particularly preferably at from −10 to 50° C., and under atmospheric pressure.

The reaction time is not critical and can be chosen from a relatively wide range, depending on the batch size.

According to the invention, the ring closure to the pyrazole is carried out in the presence of an acid. Here, the carbonyl compound $R^8R^9C=O$ is cleaved off. The carbonyl compounds can be separated off and recycled into the preparation of hydrazones of the formula (III).

Usually, step (D) is carried out after step (A), (B) or (C) without a change of solvent.

Ideally, all reaction steps of the process according to the invention are carried out in the same solvent.

Suitable solvents are, for example, aliphatic, alicyclic or aromatic hydrocarbons, such as, for example, petroleum ether, n-hexane, n-heptane, cyclohexane, methylcyclohexane, benzene, toluene, xylene or decaline, and halogenated hydrocarbons, such as, for example, chloro-benzene, dichlorobenzene, dichloromethane, chloroform, carbon tetrachloride, dichloroethane or trichloroethane, ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles, such as acetonitrile, propionitrile, n- or isobutyronitrile or benzonitrile; ketones, such as acetone, methyl ethyl ketone, methyl isobutyl ketone or cyclohexanone; amides, such as N,N-dimethylformamide, N,N-dimethylacetamide, N-methylformanilide, N-methylpyrrolidone or hexamethylphosphoric triamide; sulphoxides, such as dimethyl sulphoxide, or sulphones, such as sulpholane; alcohols, such as methanol, ethanol, n- or isopropanol, butanol. Particular preference is given to using toluene, xylene, chlorobenzene, n-hexane, cyclohexane or methylcyclohexane, ethanol, very particularly preferably ethanol, toluene, xylene and water.

Suitable acids are selected from the group consisting of HCl, $H_2SO_4$, $CF_3COOH$, $CF_3SO_3H$, $CH_3COOH$; particular preference is given to HCl and $H_2SO_4$.

After the reaction has ended, for example, the solvents are removed and the product is isolated by filtration or initially extracted with water, the organic phase is separated off and the solvent is removed by distillation.

The process according to the invention is illustrated in more detail by the examples below. However, the examples are not to be interpreted as limiting.

PREPARATION EXAMPLES

Example 1

Ethyl 3-(difluoromethyl)-1-methyl-1H-pyrazole-4-carboxylate

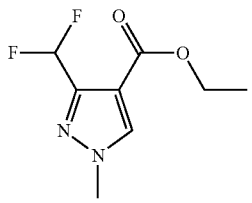

5.8 g (25 mmol) of ethyl 2-(ethoxymethylidene)-4,4-difluoro-3-oxobutanoate are initially charged in 25 ml of acetonitrile, and 2.25 g of (1-methylethylidene)hydrazone are added over a period of 5 min. The mixture is stirred at RT for 1 h, and 0.5 ml of 10% strength HCl is added. GC shows only one isomer. The mixture is concentrated and the product is washed with cold water. Yield 4.83 g (94%).

$^{19}F$-NMR ($CDCl_3$): δ=−117.2 (d) ppm.

$^1H$-NMR ($CDCl_3$): δ=1.35 (t, 3H); 3.96 (s, 3H); 4.31 (kw, 2H); 7.10 (t, 1H), 8.15 (s, 1H) ppm.

Example 2

In a departure from Example 1, methyl 2-(1-methylethylidene)hydrazone is used.

Yield 92%.

Example 3

48.8 g of 1,1,2,2-tetrafluoroethyldimethylamine are initially charged in 500 ml of acetonitrile, and 330 g of $BF_3$ (19% strength solution in $CH_3CN$) are added slowly. Subsequently, 55 g of ethyl 3-[1-methyl-2-(1-methylethylidene)hydrazino] prop-2-enoate are metered in over a period of 15-20 min, and the mixture is stirred at RT for 1.5 h. 1 ml of HCl is added to the mixture, and the acetonitrile is removed under reduced pressure. The light-yellow precipitate formed is washed with water and dried. Yield: 58 g, (94% of theory), m.p. 64-65° C., w.w. % 99%.

Example 4

Ethyl 3-(chlorofluoromethyl)-1-methyl-1H-pyrazole-4-carboxylate

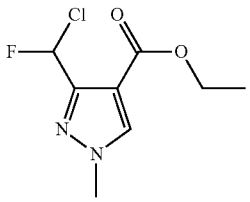

In a departure from Example 1,2-(ethoxymethylidene)-4-chloro-4-fluoro-3-oxobutanoate is used.

$^{19}F$-NMR ($CDCl_3$): δ=−133.8 (d, J=47.5) ppm.

Example 5

Ethyl 4,4-difluoro-2-{[1-methyl-2-(phenylmethylidene)hydrazino]-methylidene}-3-oxobutanoate

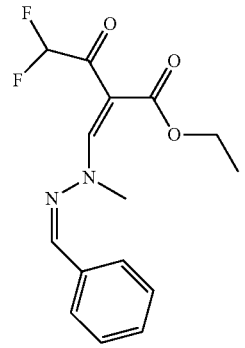 [SMILES: CCOC(=O)/C(=C\N(C)/N=C\c1ccccc1)C(=O)C(F)F]

6.2 g of 2-methyl-1-phenylhydrazone and 9.3 g of ethyl 2-(difluoroacetyl)-3-(dimethyl-amino)acrylate are initially charged in 100 ml of toluene, and 5.7 g of potassium bisulphate are added. The reaction mixture is then heated at 35-40° C. and stirred at the same temperature for 8 h. The salts are separated off, and the solvent is then removed under reduced pressure. This gives ethyl 4,4-difluoro-2-{[1-methyl-2-(phenylmethylidene)hydrazino]methylidene}-3-oxobutanoate as a solid (91% yield). The isomer ratio according to NMR is 53/39%.

$^1H$-NMR (278 K, $CDCN_3$): δ=1.08 (t, 3H); 1.23 (t, 3H); 3.44 (s, 3H); 3.52 (s, 3H); 4.14 (m, 2H); 6.0 (t, 1H); 6.37 (t, 1H); 7.4-7.98 (m, 7H) ppm.

The invention claimed is:

1. A process for preparing a 1-alkyl-3-haloalkylpyrazole-4-carboxylic acid derivative of formula (I)

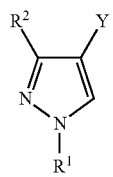

(I)

in which
R$^1$ is C$_{1-12}$-alkyl, which is optionally substituted by one or more groups selected from the group consisting of —R', —X', —OR', —SR', —NR'$_2$, —SiR'$_3$, —COOR', —(C=O)R', —CN and —CONR'$_2$, where R' is hydrogen or a C$_{1-12}$-alkyl group and X' is F, Cl, Br, or I;

R$^2$ is a C$_1$-C$_4$-alkyl group which is optionally substituted by one, two or three halogen atoms selected from the group consisting of F, Cl and Br or by a CF$_3$ group;

Y is (C=O)OR$^3$, where R$^3$ is selected from the group consisting of C$_{1-12}$-alkyl, C$_{3-8}$-cycloalkyl, C$_{2-12}$-alkenyl, C$_{2-12}$-alkynyl, C$_{6-8}$-aryl, C$_{7-19}$-aryl-alkyl and C$_{7-19}$-alkylaryl, each of which is optionally substituted by one or more groups selected from the group consisting of —R', —X', OR', —SR', —NR'$_2$, —SiR'$_3$, —COOR', —(C=O)R', —CN and —CONR'$_2$, where R' is hydrogen or a C$_{1-12}$-alkyl group and X' is F, Cl, Br, or I;

comprising at least one of the reaction sequences consisting of steps (A) and (D), (B) and (D) or (C) and (D) below:

(A) reaction of a 2-acylated or 2-iminoalkylated acrylic acid derivative of formula (II),

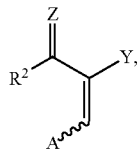

(II)

in which
Z is selected from the group consisting of O, S and N$^+$R$^{10}$R$^{11}$, where R$^{10}$ and R$^{11}$ independently of one another are selected from the group consisting of C$_{1-12}$-alkyl, C$_{3-8}$-cycloalkyl, C$_{2-12}$-alkenyl, C$_{2-12}$-alkynyl, C$_{6-8}$-aryl, C$_{7-19}$-arylalkyl and C$_{7-19}$-alkylaryl groups, each of which is optionally substituted by one or more groups selected from the group consisting of —R', —X', —OR', —SR', —NR'$_2$, —SiR'$_3$, —COOR', —(C=O)R', —CN and —CONR'$_2$, where R' is hydrogen or a C$_{1-12}$-alkyl group, X' is F, Cl, Br, or I, and R$^{10}$ and R$^{11}$ together with the nitrogen atom to which they are attached optionally form a 5- or 6-membered ring which optionally contains one or two further heteroatoms selected from the group consisting of O, S and an SO$_2$ group and which is optionally substituted by one or more groups selected from the group consisting of —R', —X', —OR', —SR', —NR'$_2$, —SiR'$_3$, —COOR', —(C=O)R', —CN and —CONR'$_2$, where R' is hydrogen or a C$_{1-12}$-alkyl group, and X' is F, Cl, Br, or I;

A is a leaving group NR$^{12}$R$^{13}$, where R$^{12}$ and R$^{13}$ independently of one another are selected from the group consisting of C$_{1-12}$-alkyl, C$_{3-8}$-cycloalkyl, C$_{2-12}$-alkenyl, C$_{2-12}$-alkynyl, C$_{6-8}$-aryl, C$_{7-19}$-aryl-alkyl and C$_{7-19}$-alkylaryl each of which is optionally substituted by one or more groups selected from the group consisting of —R', —X', —OR', —SR', —NR'$_2$, —SiR'$_3$, —COOR', —(C=O)R', —CN and —CONR'$_2$, where R' is hydrogen or a C$_{1-12}$-alkyl group, X' is F, Cl, Br, or I, and R$^{12}$ and R$^{13}$ together with the nitrogen atom to which they are attached optionally form a 5- or 6-membered ring which optionally contains one or two further heteroatoms selected from the group consisting of O, S and an SO$_2$ group and which is optionally substituted by one or more groups selected from the group consisting of —R', —X', —OR', —SR', —NR'$_2$, —SiR'$_3$, —COOR', —(C=O)R', —CN and —CONR'$_2$, where R' is hydrogen or a C$_{1-12}$-alkyl group and X' is F, Cl, Br, or I;

with an N-alkylhydrazone of formula (III)

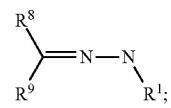

(III)

in which
R$^8$ and R$^9$ independently of one another are selected from the group consisting of C$_{1-12}$-alkyl, C$_{3-8}$-cycloalkyl, C$_{2-12}$-alkenyl, C$_{2-12}$-alkynyl, C$_{6-8}$-aryl, C$_{7-19}$-aryl alkyl and C$_{7-19}$-alkylaryl, each of which is optionally substituted by one or more groups selected from the group consisting of —R', —X', —OR', —SR', —NR'$_2$, —SiR'$_3$, —COOR', —(C=O)R', —CN and —CONR'$_2$, where R' is hydrogen or a C$_{1-12}$-alkyl group, X' is F, Cl, Br, or I, and R$^8$ and R$^9$ together with the carbon atom to which they are attached optionally form a 5- or 6-membered ring which optionally contains one or two further heteroatoms selected from the group consisting of O, S and an SO$_2$ group and which is optionally substituted by one or more groups selected from the group consisting of —R', —X', —OR', —SR', —NR'$_2$, —SiR'$_3$, —COOR', —(C=O)R', —CN and —CONR'$_2$, where R' is hydrogen or a C$_{1-12}$-alkyl group and X' is F, Cl, Br, or I;

(B) acylation of an acrylic acid hydrazone of formula (VI);

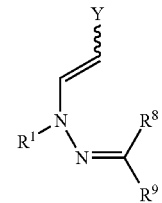

(VI)

with an acyl halide of formula (X), where X' is selected from the group consisting of F, Cl, Br and I:

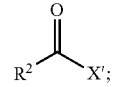

(X)

(C) iminoalkylation of an acrylic acid hydrazone of the formula (VI) above with an α,α-dihaloamine of formula (XI), where X' is selected from the group consisting of F, Cl, Br and I:

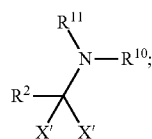

(XI)

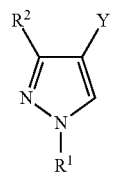

(I)

(D) cyclization of an intermediate obtained in step (A), (B) or (C) to give the 3-haloalkylpyrazole-4-carboxylic acid derivative of the formula (I).

2. The process according to claim 1, wherein the reaction sequence consists of steps (A) and (D).

3. The process according to claim 1, wherein the reaction sequence consists of steps (B) and (D).

4. The process according to claim 1, wherein the reaction sequence consists of steps (C) and (D).

5. The process according to claim 1, wherein the acyl halide of the formula (X) in step (B) is selected from the group consisting of difluoroacetyl fluoride and difluoroacetyl chloride.

6. The process according to claim 1, wherein the α,α-dihaloamine of the formula (XI) in step (C) is 1,1,2,2-tetrafluoroethyl-N,N-dimethylamine.

7. The process according to claim 1, wherein the 2-acylated or 2-iminoalkylated acrylic acid derivative of the formula (II) is selected from the group consisting of N-1-(trifluoromethyl)-3-(dimethylamino)-2-(ethoxycarbonyl)prop-2-en-1-ylidene]-N-methyl-methanaminium chloride, N-1-(difluoromethyl)-3-(dimethylamino)-2-(ethoxy-carbonyl)prop-2-en-1-ylidene]-N-methylmethanaminium tetrafluoroborate and N-[3-(dimethylamino)-2-(ethoxycarbonyl)-1-(1,1,2,2-tetrafluoroethyl)prop-2-en-1-ylidene]-N-methylmethanaminium chloride.

8. The process according to claim 1, wherein the N-alkylhydrazone of the formula (III) is selected from the group consisting of 1-methyl-2-(1-methylethylidene)hydrazine, 1-methyl-2-(1phenyl ethylidene)hydrazine, 1-methyl-2-(1,2,2-trimethylpropylidene)hydrazine, 1-methyl-2-(1-methylpropylidene)hydrazine, 1-cyclohexylidene-2-methylhydrazine, 1-methyl-2-(phenylmethylidene)hydrazine, 1-(diphenylmethyl-idene)-2-methylhydrazine, and ethyl 2-[(dimethylamino)methylidene]-4,4,4-tri-fluoro-3-oxobutanoate.

9. The process according to claim 1, wherein the acrylic acid hydrazone of the formula (VI) in steps (B) and (C) is selected from the group consisting of ethyl (2E)-3-[1-methyl-2-(propan-2-ylidene)hydrazinyl]prop-2-enoate, ethyl (2Z)-3-[1-methyl-2-(propan-2-ylidene)hydrazinyl]prop-2-enoate, methyl 3-[1-methyl-2-(propan-2-ylidene)hydrazinyl]prop-2-enoate, propyl 3-[1-methyl-2-(propan-2-ylidene)hydrazinyl]prop-2-enoate, ethyl (2E)-3-[1-methyl-2-(3,3-dimethylbutan-2-ylidene)hydrazinyl]prop-2-enoate, methyl 3-[1-methyl-2-(3,3-dimethylbutan-2-ylidene)hydrazinyl]prop-2-enoate, methyl 3-[1-methyl-2-(phenylmethylidene)-hydrazinyl]prop-2-enoate, (2E)-3-[1-methyl-2-(phenylmethyl idene)hydrazinyl]-prop-2-enenitrile and methyl 3-[1-ethyl-2-(propan-2-ylidene)hydrazinyl]prop-2-enoate.

10. A process for preparing a 1-alkyl-3-haloalkylpyrazole-4-carboxylic acid derivative of formula (I)

in which
$R^1$ is $C_{1-4}$-alkyl;
$R^2$ is a $C_1$-$C_4$-alkyl group which is optionally substituted by one, two or three halogen atoms selected from the group consisting of F, Cl and Br or by a $CF_3$ group;
is $(C=O)OR^3$, where $R^3$ is selected from the group consisting of $C_{1-12}$-alkyl, $C_{3-8}$-cycloalkyl, $C_{6-8}$-aryl, $C_{7-19}$-arylalkyl and $C_{7-19}$-alkylaryl groups; comprising;
(a) reaction of a 2-acylated or 2-iminoalkylated acrylic acid derivative of formula (II),

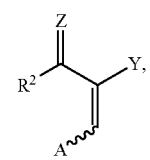

(II)

in which
Z is selected from the group consisting of O, S and $N^+R^{10}R^{11}$, where $R^{10}$ and $R^{11}$ independently of one another are selected from the group consisting of $C_{1-12}$-alkyl or $R^{10}$ and $R^{11}$ together with the nitrogen atom to which they are attached optionally form a 5- or 6-membered ring;
A is a leaving group $NR^{12}R^{13}$, where $R^{12}$ and $R^{13}$ independently of one another are selected from $C_{1-12}$-alkyl, or $R^{12}$ and $R^{13}$ together with the nitrogen atom to which they are attached optionally form a 5- or 6-membered ring;
with an N-alkylhydrazone of formula (III)

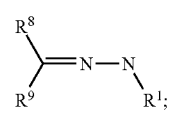

(III)

in which
$R^8$ and $R^9$ independently of one another are selected from the group consisting of hydrogen, $C_{1-12}$-alkyl, $C_{3-8}$-cycloalkyl, $C_{6-18}$-aryl, $C_{7-19}$-arylalkyl and $C_{7-19}$-alkylaryl groups, or $R^8$ and $R^9$ together with the carbon atom to which they are attached optionally form a 5- or 6-membered ring;
to form an intermediate; and
(b) cyclization of the intermediate obtained in step (a) to give the 3-haloalkylpyrazole-4-carboxylic acid derivative of the formula (I).

11. The process according to claim 10, wherein:
R' is methyl, ethyl, n-propyl, iso-propyl, n-butyl, sec-butyl, or tert-butyl;
$R^8$ is selected from the group consisting of hydrogen, methyl, ethyl, n-propyl, iso-propyl, n-butyl, sec-butyl, tert-butyl, phenyl, tolyl, and cyclohexyl;

$R^9$ is selected from the group consisting of hydrogen, methyl, ethyl, n-propyl, iso-propyl, n-butyl, sec-butyl, tert-butyl, phenyl, tolyl, and cyclohexyl,
wherein $R^8$ and $R^9$, together with the C-atom to which they are bound, optionally form a 5- or 6-membered ring.

* * * * *